United States Patent
Iwasaki et al.

(10) Patent No.: US 11,590,452 B2
(45) Date of Patent: Feb. 28, 2023

(54) METHOD FOR FILTERING PROTEIN-CONTAINING LIQUID

(71) Applicant: Asahi Kasei Medical Co., Ltd., Tokyo (JP)

(72) Inventors: Takuma Iwasaki, Tokyo (JP); Yoshiro Yokoyama, Tokyo (JP)

(73) Assignee: ASAHI KASEI MEDICAL CO., LTD., Tokyo (JP)

( * ) Notice: Subject to any disclaimer, the term of this patent is extended or adjusted under 35 U.S.C. 154(b) by 406 days.

(21) Appl. No.: 16/618,907

(22) PCT Filed: Jun. 5, 2018

(86) PCT No.: PCT/JP2018/021574
§ 371 (c)(1),
(2) Date: Dec. 3, 2019

(87) PCT Pub. No.: WO2018/230397
PCT Pub. Date: Dec. 20, 2018

(65) Prior Publication Data
US 2020/0094190 A1    Mar. 26, 2020

(30) Foreign Application Priority Data
Jun. 12, 2017 (JP) .............................. JP2017-115076

(51) Int. Cl.
| | | |
|---|---|---|
| B01D 61/14 | (2006.01) | |
| B01D 61/16 | (2006.01) | |
| B01D 61/18 | (2006.01) | |
| B01D 61/58 | (2006.01) | |
| B01D 63/08 | (2006.01) | |
| B01D 69/12 | (2006.01) | |
| C07K 16/00 | (2006.01) | |
| B01D 65/02 | (2006.01) | |
| B01D 71/34 | (2006.01) | |
| B01D 71/56 | (2006.01) | |
| B01D 71/68 | (2006.01) | |

(52) U.S. Cl.
CPC .......... *B01D 61/18* (2013.01); *B01D 61/146* (2022.08); *B01D 61/16* (2013.01); *B01D 61/58* (2013.01); *B01D 63/08* (2013.01); *B01D 65/02* (2013.01); *B01D 69/12* (2013.01); *B01D 71/34* (2013.01); *B01D 71/56* (2013.01); *B01D 71/68* (2013.01); *C07K 16/00* (2013.01)

(58) Field of Classification Search
CPC ...... B01D 61/142; B01D 61/18; B01D 61/58; C07K 16/00
See application file for complete search history.

(56) References Cited

U.S. PATENT DOCUMENTS

| | | |
|---|---|---|
| 5,891,340 A | 4/1999 | Akiyama et al. |
| 2003/0146156 A1 | 8/2003 | Siwak |
| 2004/0023017 A1 | 2/2004 | Nagoya |
| 2006/0054557 A1 | 3/2006 | Hori |
| 2013/0056415 A1 | 3/2013 | Kozlov |
| 2014/0199262 A1 | 7/2014 | Hongo |
| 2014/0309403 A1 | 10/2014 | Brown |
| 2015/0367291 A1 | 12/2015 | Hornung et al. |
| 2016/0115194 A1* | 4/2016 | Gagnon .................. C07K 1/30 435/334 |
| 2016/0176921 A1 | 6/2016 | Rajendran et al. |
| 2017/0029462 A1 | 2/2017 | Hamamoto et al. |

FOREIGN PATENT DOCUMENTS

| | | |
|---|---|---|
| CN | 101027080 A | 8/2007 |
| CN | 102333583 | 1/2012 |
| CN | 103608352 | 2/2014 |
| CN | 104321133 A | 1/2015 |
| EP | 2412817 | 2/2012 |
| JP | H08-164328 | 6/1996 |
| JP | 2001-120960 | 5/2001 |
| JP | 2004-277323 | 10/2004 |
| JP | 2012-519065 | 8/2012 |
| WO | 1999/064441 | 12/1999 |
| WO | 2003/026779 | 4/2003 |
| WO | 2004/052270 | 6/2004 |
| WO | 2012/176876 | 12/2012 |

(Continued)

OTHER PUBLICATIONS

Rosenberg, E., et al. "Ultrafiltration concentration of monoclonal antibody solutions: Development of an optimized method minimizing aggregation." Journal of Membrane Science 342.1-2 (2009): 50-59. (Year: 2009).*
Hongo-Hirasaki, Tomoko, Masayasu Komuro, and Shoichi Ide. "Effect of antibody solution conditions on filter performance for virus removal filter Planova™ 20N." Biotechnology progress 26.4 (2010): 1080-1087. (Year: 2010).*
Supplementary European Search Report, European Patent Office, Application No. 18818937.7, dated Mar. 24, 2020.
Brough H et al., Performance of a Novel Viresolve NFR Virus Filter, Biotechnology Progress, American Chemical Society, vol. 18, No. 4, 2002, pp. 782-795.

(Continued)

Primary Examiner — Bradley R Spies
(74) Attorney, Agent, or Firm — Greenblum & Bernstein, P.L.C.

(57) ABSTRACT

A method for filtering a protein-containing liquid containing protein at a concentration of 20 mg/mL or more and 100 mg/mL or less, the method including a prefiltration step of filtering the protein-containing liquid by a prefilter having a pore size of 0.08 μm to 0.25 μm and including a hydrophobic resin, and a virus removal step of filtering the protein-containing liquid by a virus removal membrane including a synthetic polymer, after the prefiltration step, wherein the protein-containing liquid before conducting the prefiltration step includes 0.25 g or more of a trimer or higher multimer of the proteins having an average diameter of less than 100 nm, per 1 m² of the virus removal membrane.

29 Claims, 14 Drawing Sheets

(56) References Cited

FOREIGN PATENT DOCUMENTS

WO  2015/156403     10/2015
WO  2016/154290 A1  9/2016

OTHER PUBLICATIONS

Bolton R et al., Increasing the Capacity of Parvovirus-Retentive Membranes: Performance of the Viresolve (TM) Prefilter, Biotechnology and Applied Biochemistry, Academic Press, vol. 43, 2006, pp. 55-63.
International Search Report, WIPO, PCT/JP2018/021574, dated Sep. 4, 2018, and its English Translation.
International Preliminary Report on Patentability, WIPO, PCT/JP2018/021574, dated Dec. 17, 2019, and its English Translation.
Manabe. S, Removal of virus through novel membrane filtration method., Dev. Biol. Stand., (1996)88: 81-90.
Brandwein H et al., Menbrane filtration for virus removal., Dev Biol (Basel)., (2000)102: 157-63.
Aranha-Creado et al., Clearance of murine leukaemia virus from monoclonal antibody solution by a hydrophilic PVDF microporous membrane filter., Biologicals., Jun. 1998; 26(2):167-72.
L. Moce-Llivina et al, Comparison of polyvinylidene fluoride aqnd polyether sulfone membranes in filtering viral suspensions, Journal of Virological Methods, 2003, vol. 109, Issue 1, pp. 99-101.

* cited by examiner

Fig. 5

|  |  |  | EXAMPLE 1 | EXAMPLE 2 | EXAMPLE 3 | EXAMPLE 4 | EXAMPLE 5 | EXAMPLE 6 | EXAMPLE 7 | EXAMPLE 8 | EXAMPLE 9 | EXAMPLE 10 | EXAMPLE 11 |
|---|---|---|---|---|---|---|---|---|---|---|---|---|---|
| PRODUCTION CONDITIONS | HOLLOWING AGENT INLET TEMPERATURE |  | °C | 95.0 | 80.0 | 62.5 | 80.0 | 62.5 | 62.5 | 62.5 | 55.0 | 80.0 | 62.5 | 62.5 |
|  | HOLLOWING AGENT OUTLET TEMPERATURE |  | °C | 155.0 | 150.0 | 140.0 | 150.0 | 140.0 | 140.0 | 140.0 | 135.0 | 450.0 | 140.5 | 140.5 |
|  | DIFFERENCE IN HOLLOWING AGENT TEMPERATURE (OUTLET-INLET) |  | °C | 60.0 | 70.0 | 77.5 | 70.0 | 77.5 | 77.5 | 77.5 | 80.0 | 70.0 | 77.5 | 77.5 |
|  | COAGULATING BATH TEMPERATURE |  | °C | 21.0 | 22.0 | 25.0 | 25.5 | 25.0 | 26.0 | 26.0 | 30.0 | 24.0 | 26.0 | 30.0 |
|  | AIR GAP |  | mm | 200 | 150 | 100 | 50 | 50 | 50 | 50 | 50 | 30 | 30 | 30 |
| PHYSICAL PROPERTIES | GRAFT RATIO |  | % | 8.7 | 10.1 | 8.8 | 9.6 | 9.5 | 10.1 | 10.2 | 9.5 | 9.5 | 9.1 | 9.0 |
|  | INNER DIAMETER |  | µm | 340.0 | 329.0 | 328.0 | 337.0 | 334.0 | 335.0 | 327.0 | 329.0 | 329.0 | 327.0 | 328.0 |
|  | THICKNESS |  | µm | 45.0 | 48.0 | 46.0 | 48.0 | 48.0 | 45.0 | 48.0 | 48.0 | 43.0 | 43.5 | 43.2 |
|  | BUBBLE POINT |  | MPa | 1.80 | 1.73 | 1.60 | 1.59 | 1.57 | 1.50 | 1.51 | 1.40 | 1.50 | 1.46 | 1.38 |
|  | PURE WATER PERMEATION RATE |  | L/m²/hrs/0.1MPa | 33 | 35 | 38 | 43.9 | 40 | 46 | 44 | 54.8 | 45 | 50 | 54 |
| EVALUATIONS | THICKNESS OF DENSE LAYER |  | µm | 10.4 | 10.0 | 10.1 | 15.2 | 15.1 | 16.4 | 13.9 | 17.2 | 25.0 | 26.4 | 24.8 |
|  | VARIATION COEFFICIENT OF AMOUNT OF CAPTURED GOLD COLLOIDS |  |  | 0.28 | 0.50 | 0.80 | 0.39 | 0.59 | 0.44 | 0.73 | 1.30 | 0.32 | 0.66 | 0.87 |
|  | THICKNESS OF DENSEST LAYER |  | µm | 9.6 | 8.8 | 7.7 | 7.8 | 4.6 | 3.4 | 3.6 | 3.4 | 3.7 | 2.8 | 2.4 |
|  | FIRST ATTAINMENT LEVEL, SECOND ATTAINMENT LEVEL | 30 nm | % | 37~42 | 38~43 | 36~44 | 28~41 | 34~42 | 30~43 | 30~41 | 29~41 | 16~41 | 18~40 | 20~39 |
|  |  | 20 nm | % | 39~63 | 40~62 | 43~60 | 36~65 | 43~69 | 42~70 | 40~63 | 40~70 | 43~77 | 45~80 | 43~79 |
|  |  | 15 nm | % | 74~98 | 78~99 | 80~99 | 76~95 | 87~98 | 90~98 | 89~97 | 90~98 | 89~98 | 93~100 | 93~99 |
|  | LOGARITHMIC REMOVAL RATE OF GOLD COLLOID | 30 nm | LRV | ≥1.40 | ≥1.40 | ≥1.40 | ≥1.40 | ≥1.40 | ≥1.40 | ≥1.40 | ≥1.40 | ≥1.40 | ≥1.40 | ≥1.40 |
|  |  | 20 nm | LRV | ≥1.40 | ≥1.40 | ≥1.40 | ≥1.40 | ≥1.40 | ≥1.40 | ≥1.40 | ≥1.40 | ≥1.40 | ≥1.40 | ≥1.40 |
|  |  | 15 nm | LRV | ≥1.40 | ≥1.40 | ≥1.40 | ≥1.40 | 1.20 | 1.10 | 0.92 | 0.50 | 0.60 | 0.40 | 0.30 |
|  |  | 10 nm | LRV | 0.09 | 0.08 | 0.07 | 0.07 | 0.05 | 0.05 | 0.05 | 0.04 | 0.04 | 0.04 | 0.03 |
| EFFECTS | VIRUS REMOVAL PROPERTY |  | LRV | ≥6.00 | ≥6.00 | ≥6.00 | ≥6.00 | ≥6.00 | ≥6.00 | ≥6.00 | ≥6.00 | ≥6.00 | ≥6.00 | ≥6.00 |
|  | LRV IF STOP AND START |  | LRV | ≥6.00 | ≥6.00 | ≥6.00 | ≥6.00 | ≥6.00 | 5.00 | 5.00 | 4.50 | 4.50 | 4.30 | 4.10 |
|  | MAXIMUM CAPTURE CAPACITY |  | Log₁₀(TCID₅₀/M²) | ≥14.0 | ≥13.8 | 13.5 | 13.5 | 13.3 | 13.1 | 12.8 | 12.3 | 12.5 | 12.2 | 11.8 |

① TRIMER OR HIGHER MULTIMER
② DIMER
③ MONOMER

Fig. 9

| | CONCENTRATION OF MULTIMER ADDED | AMOUNT OF MULTIMER PER SQUARE METER OF VIRUS REMOVAL MEMBRANE | PREFILTER | MATERIAL OF PREFILTER | TIME TAKEN FOR FILTRATION BY VIRUS REMOVAL MEMBRANE |
|---|---|---|---|---|---|
| | μg/25mL | g/m² | | | hr/(2.5kg/m²) |
| EXAMPLE 1 | 0.30 | 1.00 | Durapore | PVDF | 1.08 |
| COMPARATIVE EXAMPLE 1 | 0.30 | 1.00 | NONE | — | >4900 |
| EXAMPLE 2 | 1.03 | 3.40 | Virosart Max | POLYAMIDE | 2.13 |
| COMPARATIVE EXAMPLE 2 | 1.03 | 3.40 | NONE | — | >150000 |
| EXAMPLE 3 | 0.15 | 0.50 | Supor | PES | 3.00 |
| COMPARATIVE EXAMPLE 3 | 0.15 | 0.50 | NONE | — | 1850 |
| EXAMPLE 4 | 0.30 | 1.00 | SYRINGE FILTER NY | NYLON | 47 |
| COMPARATIVE EXAMPLE 4 | 0.30 | 1.00 | NONE | — | >4900 |

Fig. 14

| | CONCENTRATION OF MULTIMER ADDED | AMOUNT OF MULTIMER PER SQUARE METER OF VIRUS REMOVAL MEMBRANE | PREFILTER | MATERIAL OF PREFILTER | TIME TAKEN FOR FILTRATION BY VIRUS REMOVAL MEMBRANE |
|---|---|---|---|---|---|
| | μg/25mL | g/m² | | | hr/(2.5kg/m2) |
| EXAMPLE 5 | 1.03 | 3.40 | Durapore | PVDF | 1.40 |
| EXAMPLE 6 | 1.03 | 3.40 | Virosart Max | POLYAMIDE | 5.67 |
| COMPARATIVE EXAMPLE 5 | 1.03 | 3.40 | NONE | — | >150000 |

METHOD FOR FILTERING PROTEIN-CONTAINING LIQUID

TECHNICAL FIELD

The present invention relates to a method for filtering a protein-containing liquid.

BACKGROUND ART

In recent years, a measure to enhance virus safety has been necessary for not only plasma derivatives derived from human blood, but also bio-pharmaceuticals. Therefore, pharmaceutical manufacturers have studied to introduce a virus removal/inactivation step in a manufacturing process. In particular, a virus removal method by filtration with a virus removal membrane is an effective method that can provide virus reduction without denaturing useful proteins.

Among viruses, in particular, parvovirus has been reported with respect to a case of infection with human parvovirus B19 in the field of plasma derivatives, and a case of contamination of CHO (Chinese Hamster Ovary) cells with mouse parvovirus in the bio-pharmaceutical field. In addition, a case has also been reported where microbacteria such as Leptospira species remain in bio-pharmaceuticals.

Parvovirus, which is a small virus, has no envelope, and it is thus physicochemically stable and is resistant to heating, a low pH and a treatment with a chemical agent which correspond to an inactivation step generally performed during a pharmaceutical manufacturing process. Therefore, there are growing needs for virus removal and bacteria removal by a virus removal membrane, as a virus removal method having a different mechanism from that of an inactivation method.

As filtration membrane for virus removal, membranes including a natural material like cellulose, and virus removal membranes including a synthetic polymer material like polyvinylidene fluoride (PVDF) or polyether sulfone (PES) have been known (see, for example, Patent Literatures 1 and 2, and Non Patent Literatures 1 to 4.). A virus removal membrane having high virus removal properties with respect to a small virus (for example, parvovirus) having a size close to the size of a useful protein and also having high protein filtration efficiency has been demanded in the pharmaceutical manufacturing site, and the demand for a virus removal membrane has been increasingly severe year by year.

CITATION LIST

Patent Literature

Patent Literature 1: Japanese Patent Laid-Open No. 2004-277323
Patent Literature 2: U.S. Patent Application Publication No. 2016/0176921

Non Patent Literature

Non Patent Literature 1: Manabe.S, Removal of virus through novel membrane filtration method., Dev. Biol. Stand., (1996)88: 81-90.
Non Patent Literature 2: Brandwein H et al., Membrane filtration for virus removal., Dev Biol (Basel)., (2000)102: 157-63.
Non Patent Literature 3: Aranha-Creado et al., Clearance of murine leukaemia virus from monoclonal antibody solution by a hydrophilic PVDF microporous membrane filter., Biologicals. (1998) Jun.; 26(2): 167-72.
Non Patent Literature 4: L. Moce-Llivina et al., Comparison of polyvinylidene fluoride and polyether sulfone membranes in filtering viral suspensions, Journal of Virological Methods, (2003) April, Vol. 109, Issue 1, Pages 99-101.

SUMMARY OF INVENTION

Technical Problem

In recent years, there has been increasingly concerned about the occurrence of risk of contamination with microbacteria such as Leptospira licerasiae and viruses at a high probability in a final purification step of a biological medicine where CHO is utilized for host cells. There are not a few preparations as antibody drugs, which are concentrated from a concentration of 20 mg/mL to a concentration of 100 mg/mL through a final ultrafiltration/diafiltration (UF/DF) step and thereafter filtered by use of a sterilization membrane having a pore size of 0.22 µm. Such a step is not necessarily performed in aseptic conditions, but is performed in a non-sterilized environment manually set-up, and thus there are concerns about the occurrence of contamination resulting from an operator, and the occurrence of contamination resulting from microbacteria and viruses in final preparation of buffer. Such a final UF/DF step in a pharmaceutical manufacturing process, however, is generally performed after a virus removal step by a virus removal membrane, and thus microbacteria and viruses cannot be removed in such a final UF/DF step and a subsequent 0.22-µm-sterilization membrane step. The present inventors have found from such viewpoints that a step of removing microbacteria and viruses after such a final UF/DF step is useful for realization of safe pharmaceutical manufacturing.

A high-concentration protein solution obtained in the final UF/DF step may include a multimer formed by association of monomers of proteins contained. In particular, aggregation of proteins may be promoted by shear stress in the above purification step as in UF/DF, causing the multimer to expand to a visible particulate substance. A multimer of proteins contained in a pharmaceutical drug is known to cause side effects on human bodies, and it is preferred to remove the multimer. Furthermore, such multimer and particulate substance cause occlusion of a virus removal membrane for use after the final UF/DF step. Such multimer and particulate substance, however, are generally said to be difficult to remove by a 0.22-nm-sterilization membrane, and removal of such a multimer after the above purification step as in ultrafiltration or the like has not been heretofore sufficiently studied.

Accordingly, it is ideal for filtration of a protein preparation intermediate product by a virus removal apparatus packed with a virus removal membrane to enable filtration of a larger amount of proteins in a short time, removal of multimers, and virus removal by means of sufficiently high virus removal capability. For example, however, a virus removal membrane including cellulose, while hardly causes the occurrence of clogging even in filtration of a protein solution including 0.25 g/m$^2$ or more of a multimer, causes a remarkable reduction in filtration rate in filtration of a protein solution having a high concentration of 20 mg/mL or more, and thus tends to be reduced in the amount of protein that can be filtered per unit time, as compared with the case of filtration of a low-concentration protein solution.

The present inventors have also found that a virus removal membrane including a synthetic polymer, which is high in pressure resistance and has no problem even at a practical pressure increased up to about 300 kPa, can often have the problem of being incapable of filtration due to clogging caused at a protein concentration increased to about 20 mg/mL. Thus, in the case of using such a virus removal membrane including a synthetic polymer, filtration is generally performed at a low concentration of 10 mg/mL or less (see, for example, Patent Literature 1.).

For such reasons, neither any research for a filtration method in a filtration condition where a protein preparation intermediate product having a high protein concentration increased in a purification step such as each chromatography or final ultrafiltration is allowed to flow in a virus removal apparatus at a high pressure has been progressed, nor any development for a virus removal membrane suitable for the method has been progressed. One object of the present invention is then to provide a method that can allow a protein-containing liquid that contains proteins at a high concentration to be filtered at a high efficiency.

Solution to Problem

An aspect of the present invention provides a method for filtering a protein-containing liquid containing protein at a concentration of 20 mg/mL or more and 100 mg/mL or less, the method including a prefiltration step of filtering the protein-containing liquid by a prefilter having a pore size of 0.08 μm to 0.25 μm and including a hydrophobic resin, and a virus removal step of filtering the protein-containing liquid by a virus removal membrane including a synthetic polymer, after the prefiltration step, wherein the protein-containing liquid before conducting the prefiltration step includes 0.25 g or more of a trimer or higher multimer of the proteins having an average diameter of less than 100 nm, per 1 $m^2$ of the virus removal membrane.

In the method, the prefilter may include a material selected from the group consisting of a polyamide resin, a polysulfone-based resin and a fluororesin.

In the method, the prefilter may include polyether sulfone or polyvinylidene fluoride.

In the method, the protein-containing liquid before conducting the prefiltration step may further include a particulate substance which is a multimer of the proteins and which has a diameter of 100 nm or more.

The method may further include a diafiltration step of conducting diafiltration of the protein-containing liquid, before the prefiltration step.

The method may further include an ultrafiltration step of conducting ultrafiltration of the protein-containing liquid, before the prefiltration step.

The method may not further include ultrafiltration step and diafiltration step, after the diafiltration step.

The method may further include a tangent flow filtration step of conducting filtration by use of a tangent flow filtration apparatus, before the prefiltration step.

The method may further include a stirring step of stirring the protein-containing liquid for two hours or more, before the prefiltration step.

The method may include no other step between the prefiltration step and the virus removal step.

In the method, the prefiltration step and the virus removal step may be successively performed.

In the method, the prefilter may be a sheet-shaped filter.

In the method, the prefilter may include a multi-layer membrane.

In the method, the prefilter may include a multi-layer membrane where each layer is different in filter pore size.

In the method, a viscosity of the protein-containing liquid filtered by the prefilter may be lower than a viscosity of the protein-containing liquid before filtration by the prefilter.

In the method, the protein may include an antibody. The antibody may be a monoclonal antibody.

In the method, the virus removal membrane may include polyvinylidene fluoride. A logarithmic removal rate (LRV) of parvoviruses by the virus removal membrane may be 4.0 or more.

In the method, the virus removal membrane may include a primary surface to which the protein-containing liquid filtered by the prefilter is applied, and a secondary surface from which a liquid that permeates through the virus removal membrane is flowed; in the case where a solution containing gold colloids having a diameter of 20 nm are applied through the primary surface to the virus removal membrane to allow the virus removal membrane to capture the gold colloid for measurement of brightness in a cross section of the virus removal membrane, a value obtained by dividing a standard deviation of a value of an area of a spectrum of variation in the brightness by an average of the value of the area of the spectrum of variation in the brightness may be 0.01 or more and 1.50 or less; and a thickness of a portion where gold colloids having a diameter of 20 nm or more and 30 nm or less are captured in the cross section of the virus removal membrane in a wet state may be 10 μm or more and 30 μm or less.

In the method, the protein-containing liquid before conducting the prefiltration step may have a hydrogen-ion exponent of 4.0 or more and 8.0 or less. The protein-containing liquid before conducting the prefiltration step may have an ionic strength of 0 mmol/L or more and 300 mmol/L or less. The protein-containing liquid before conducting the prefiltration step may include an additive including at least one selected from the group consisting of a sugar and a basic amino acid.

In the method, the prefilter may be sterilizable-in-place.

Advantageous Effects of Invention

The present invention makes it possible to provide a method that can allow a protein-containing liquid containing protein at a high concentration to be filtered at a high efficiency.

BRIEF DESCRIPTION OF DRAWINGS

FIG. 5 is a table showing manufacturing conditions and evaluation results of a virus removal membrane according to each Example of the present invention.

FIG. 9 is a graph representing the time taken for filtration by each virus removal membrane according to Examples of the present invention and Comparative Examples.

FIG. 14 is a graph representing the time taken for filtration by each virus removal membrane according to Examples of the present invention and Comparative Examples.

DESCRIPTION OF EMBODIMENTS

Figure 1:
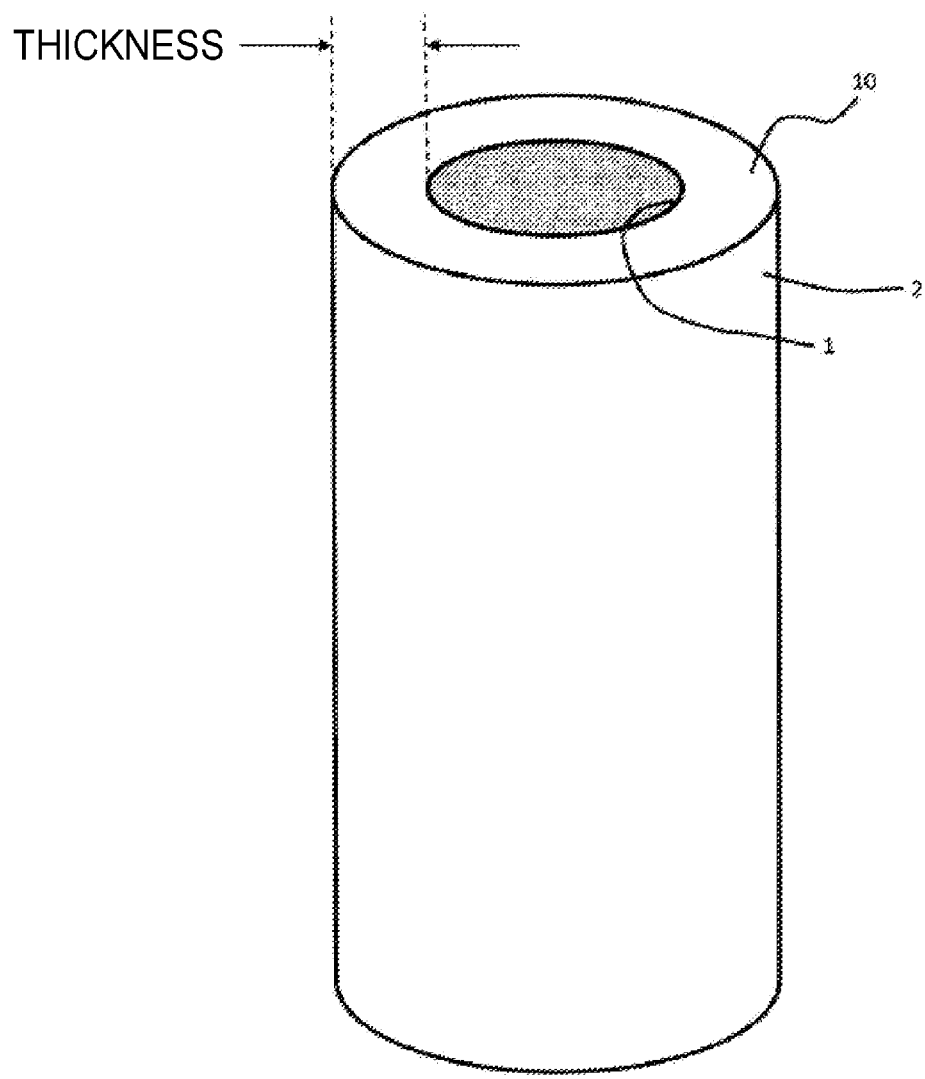
FIG. 1 is a schematic view of a virus removal membrane having a hollow fiber membrane shape, according to an embodiment of the present invention.

Hereinafter, embodiments of the present invention are described. In the following description of drawings, the same or similar part is represented by the same or similar reference sign. The drawings, however, are schematic, and are not accurately illustrated by specific dimensions and the like. Accordingly, specific dimensions and the like are required to be understood in view of the following description, and parts whose dimension relationship and ratio are different among the drawings are, of course, included.

A method for filtering a protein-containing liquid according to an embodiment of the present invention is a method for filtering a protein-containing liquid containing protein at a concentration of 20 mg/mL or more and 100 mg/mL or less, the method including a prefiltration step of filtering the protein-containing liquid by a prefilter having a pore size of 0.08 μm to 0.25 μm and comprising a hydrophobic resin, and a virus removal step of filtering the protein-containing liquid by a virus removal membrane comprising a synthetic polymer, after the prefiltration step, wherein the protein-containing liquid before conducting the prefiltration step includes 0.25 g or more of a trimer or higher multimer of the proteins having an average diameter of less than 100 nm, per 1 m$^2$ of the virus removal membrane. Bacteria may also be removed in the virus removal step.

The phrase "the protein-containing liquid before conducting the prefiltration step includes 0.25 g or more of a trimer or higher multimer of the protein having an average diameter of less than 100 nm, per 1 m$^2$ of the virus removal membrane" means that the following two requirements are satisfied.

(1) The average diameter of a trimer or higher multimer resulting from fractionation of a liquid to be treated, by use of size exclusion chromatography (SEC) or the like, as measured according to a dynamic light scattering method (DLS) is less than 100 nm.

(2) The amount of a multimer included in a liquid to be treated, as calculated from the relative area ratio calculated from the peak area of a trimer or higher multimer resulting from fractionation of the liquid to be treated, by use of size exclusion chromatography chart, the total amount of the liquid to be treated per 1 m$^2$ of the virus removal membrane, and the total protein concentration, according to the following equation (1), is 0.25 g or more.

(Amount of multimer to be included per 1 m$^2$ of virus removal membrane: g/m$^2$)=(Total amount of liquid to be treated per 1 m$^2$: L/m$^2$)×(Total protein concentration: g/L)×(Relative area ratio of trimer or higher multimer calculated from peak area of chromatography chart: %)/100    (1)

In general, it can be considered that the average diameter in a fraction including a large amount of a multimer has a normal distribution, and it can be considered that, in the case where the average diameter measured according to DLS is less than 100 nm, 50% or more of substances included in the objective solution includes particles having a diameter of less than 100 nm. Accordingly, it can be considered that most of a trimer or higher multimer of proteins included in the protein-containing liquid satisfying requirement (1) includes particles having an average diameter of less than 100 nm.

The content and the size of a trimer or higher multimer having an average diameter of less than 100 nm, included in the protein-containing liquid, can be determined by an analysis system where a unit that allows for fractionation depending on the size, such as SEC, an analysis unit that can quantitatively determine the amount of a sample obtained by fractionation, such as an UV detector, and a unit that can analyze size, such as DLS, are linked. For example, according to Reference Document (Biotechnol. Prog., 2015, Vol. 31, No. 3), the content of a multimer contained in a trace amount which cannot be detected by a single UV detector has been identified using an apparatus where SEC, an UV detector, and DLS are linked. It is noted that, if the concentration of a multimer is condensed to a high concentration by concentrating or the like of the protein-containing liquid, it is possible to quantitate the amount of a multimer by a single UV detector.

Exemplary protein here is antibody protein. Antibody protein as one example of a physiologically active substance is a glycoprotein molecule (also referred to as "gamma-globulin or immunoglobulin") that is produced by B lymphocytes as a defense mechanism against infection of vertebrate animals, as generally defined in biochemistry. For example, an antibody protein purified by an embodiment is used in pharmaceuticals for human use, and has substantially the same structure as that of an antibody protein in the human body as an administration subject.

The antibody protein may be a human antibody protein or an antibody protein derived from mammal other than human, such as cow or mouse. Alternatively, the antibody protein may be a chimeric antibody protein with human IgG, and a humanized antibody protein. Such a chimeric antibody protein with human IgG means an antibody protein where, while a variable domain is derived from living organism other than human, such as mouse, other constant domains are replaced with immunoglobulin derived from human. The humanized antibody protein means an antibody protein where, while a complementarity-determining region (CDR) in a variable domain is derived from living organism other than human, other framework regions (FR) are of human origin. The humanized antibody protein is further reduced in immunogenicity as compared with the chimeric antibody protein.

The class (isotype) and subclass of the antibody protein are not particularly limited. For example, the antibody protein is classified into five classes of IgG, IgA, IgM, IgD, and IgE, depending on the difference in constant domain structure. The antibody protein to be purified by the filtration method according to the embodiment, however, may be any of such five classes. The human antibody protein is classified into four subclasses of IgG1 to IgG4 included in IgGs, and IgA includes two subclasses of IgA1 and IgA2. The subclass of the antibody protein to be purified by the filtration method according to the embodiment, however, may be any subclass. It is noted that an antibody-related protein such as Fc fusion protein where protein is bound to an Fc domain can also be encompassed in the antibody protein to be purified by the filtration method according to the embodiment.

The antibody protein can also be classified depending on the origin. The antibody protein to be purified by the filtration method according to the embodiment, however, may be any of a natural human antibody protein, a recombinant human antibody protein produced by genetic recombination technology, a monoclonal antibody protein, and a polyclonal antibody protein. Among such antibody proteins, the antibody protein to be purified by the filtration method according to the embodiment is suitably human IgG or a monoclonal antibody from the viewpoint of demand and importance of an antibody drug, but not limited thereto.

The protein concentration of the protein-containing liquid before filtration by the prefilter is 20 mg/mL or more, or 25 mg/mL or more, and 100 mg/mL or less, 90 mg/mL or less, 80 mg/mL or less, 70 mg/mL or less, 60 mg/mL or less, or 50 mg/mL or less. The protein-containing liquid having the protein concentration of 20 mg/mL or more tends to allow a multimer of proteins, having a diameter of less than 100 nm, and particulate substances having a diameter of 100 nm or more to be easily formed. For example, a multimer of IgGs may cause serious side effects because the multimer is bound to a complement in the state of not being bound to an antigen as pathogen and thus causes the complement to be abnormally activated.

The protein-containing liquid before filtration by the prefilter may include a multimer of proteins. The multimer of proteins is formed by aggregation of a plurality of protein monomers. The multimer of proteins means, for example, a dimer and a trimer of proteins (which, by itself, may be an associated product such as a dimer). The "multimer" in the present disclosure particularly refers to a trimer or higher multimer. The protein-containing liquid before filtration by the prefilter contains proteins having an average diameter of less than 100 nm and includes 0.25 g or more, 0.35 g or more, 0.50 g or more, or 0.75 g or more of a trimer or higher multimer per 1 m$^2$ of the virus removal membrane. If the trimer or higher multimer is contained in an amount of 0.25 g or more, the effect of the prefilter, described below, tends to be easily exerted.

The protein-containing liquid before filtration by the prefilter may include viruses. The virus has, for example, a diameter of 10 nm or more and 30 nm or less, or 18 nm or more and 24 nm or less. The virus is, for example, parvovirus. The parvovirus has a diameter of about 20 nm. The protein-containing liquid before filtration by the prefilter may include bacteria. Examples of such bacteria include the genus *Leptospira*, the genus *Bacillus*, the genus *Paenibacillus*, the genus *Stenotrophomonas*, the genus *Ochrobactrum*, and the genus *Pseudomonas*.

The solvent of the protein-containing liquid before filtration by the prefilter is, for example, water or buffer. The buffer here means an aqueous solution containing a salt, and specific examples include phosphate buffer, Tris buffer and acetate buffer, but not particularly limited as long as these are each buffer commonly utilized. The protein-containing liquid before filtration by the prefilter may include, for example, sugar and/or basic amino acid as additive(s). Addition of a sugar, a basic amino acid, and/or the like can allow formation of a multimer to be inhibited, resulting in an enhancement in filtration efficiency of the virus removal membrane. The hydrogen-ion exponent (pH) of the protein-containing liquid before filtration by the prefilter is, for example, 4.0 or more and 8.0 or less, 4.0 or more and 7.5 or less, or 4.0 or more and 7.0 or less. The ionic strength of the protein-containing liquid before filtration by the prefilter is 0 mmol/L or more and 300 mmol/L or less, 10 mmol/L or more and 280 mmol/L or less, or 20 mmol/L or more and 250 mmol/L or less.

The protein-containing liquid before filtration by the prefilter is, for example, a solution subjected to any one of or both ultrafiltration (UF) and diafiltration (DF). The protein-containing liquid is, for example, subjected to any one of or both ultrafiltration and diafiltration by use of a tangent flow (cross-flow) recirculation filtration apparatus. The diavolume in diafiltration is, for example, four. The diavolume here corresponds to the ratio of the volume of a collected filtrate to the volume of a retention liquid at the initial of diafiltration. The protein-containing liquid before filtration by the prefilter may be a solution mechanically stirred, or may be a solution subjected to any one of or both ultrafiltration and diafiltration with stirring. The stirring time is, for example, two hours or more, four hours or more, or six hours or more.

When the protein-containing liquid is filtered with at least one of ultrafiltration and diafiltration, multimers of proteins having a diameter of less than 100 nm and particulate substances having a diameter of 100 nm or more tend to be easily formed. The multimers of proteins having a diameter of less than 100 nm, and the particulate substances having a diameter of 100 nm or more may be formed also by mechanical stirring in some cases. A virus inactivation step other than the filtration step by the virus removal membrane may be incorporated in a purification step of plasma derivatives, bio-pharmaceuticals, and/or the like, in order to enhance safety against viruses. Examples of a procedure for use in such a case include a heating treatment, a low-pH treatment, and a Solvent/Detergent treatment (hereinafter, sometimes also designated as "S/D treatment"). Such inactivation methods involve allowing living organisms to be chemically or physically unstable, thereby resulting in disruption of biomaterials that form virus particles, but possibly simultaneously causing objective proteins to be denatured or aggregated, thereby resulting in generation of a large amount of multimers including particulate substances having a diameter of more than 100 nm. While the multimers including the particulate substances are possibly removed before the virus removal step in the case where the S/D treatment and subsequent purification steps such as the chromatography step are performed, there is a possibility that the protein solution including the particulate substances is loaded to the virus removal membrane in the case where the S/D treatment is performed in a step near the virus removal step. The step near the virus removal step means that the S/D treatment step is performed within one or two steps upstream of the virus removal step. It is known that denatured protein causes undenatured protein present around the denatured protein to be denatured/aggregated. As the concentration of the protein solution is higher, the contact probability of denatured protein with undenatured protein is higher, thereby causing aggregation to more easily occur. A concentration of more than 30 mg/mL of the protein solution not only may cause a virus removal membrane made of a synthetic polymer to be remarkably reduced in filtration flux due to clogging, but also may result in a reduction in flux at a level where filtration can be no longer made, even in the presence of a trace amount of a multimer. For example, a multimer of IgGs may cause a serious side effect because the multimer is bound to a complement in the state of not being bound to an antigen as pathogen and causes the complement to be abnormally activated. In addition, it is said that a virus removal membrane, while does not substantially block protein, but allows protein to penetrate, separates virus and protein having a size close to each other by multiple layers stacked each having a pore size distribution that allows viruses to be partially blocked (Masanobu YOKOGI, "Virus Separation by Cellulose Hollow Fiber Membrane", Sen'i To Kogyo, vol. 55 (1999), No. 10, pages 338 to 342). If, however, particles having a size equal to or more than the size of virus, such as multimers of proteins, are present, there is a possibility that the multimers are captured in the pore having the size so that the virus is to be captured, resulting in an increase in probability where the virus is leaked into a filtrate.

The prefilter that filters the protein-containing liquid is, for example, a sheet-shaped filter. The prefilter has a pore size of 0.08 μm or more, or 0.10 μm or more, and 0.25 μm or less, or 0.20 μm or less. The prefilter comprises, for example, a hydrophobic resin such as a polyamide resin, a polysulfone-based resin, and a fluororesin. While not bound to any theory, it is presumed that such a hydrophobic resin hydrophobically interacts with a multimer of proteins and adsorbs the multimer. Polyamide (PA), polyether sulfone or polyvinylidene fluoride is preferable, and polyvinylidene fluoride is more preferable from the viewpoint of adsorption of protein. As the prefilter has the pore size of 0.08 μm or more, it is possible to filtrate protein monomers in the protein-containing liquid at a high permeability, resulting in an enhancement in recovery rate of the proteins. The prefilter has a larger pore size than that of the multimer, thereby enabling the prefilter to be inhibited from clogging due to the multimer at the early stage. Furthermore, the prefilter has hydrophobic interaction, thereby allowing the trimer or higher multimer of proteins in the protein-containing liquid to be removed even in the case where the prefilter has the larger pore size than the size of the multimer, resulting in enhancements in subsequent filtration efficiency and virus removal properties of the virus removal membrane. If particulate substances are included in the solution, the multimers located around the particulate substances may be brought into contact with the particulate substances and thus removed by the prefilter together with the particulate substances, resulting in enhancements in filtration flux and virus removal capability of the virus removal membrane. The prefilter has a pore size of 0.25 μm or less, resulting in an increase in specific surface area and an increase in contact area with the multimers, thereby enabling the adsorption area of the multimers to be sufficiently ensured. In the case where the protein-containing liquid includes a large amount of the multimers, the prefilter may be used in combinations of two or more kinds thereof, or a plurality thereof may be connected. In such a case, the total area required for the prefilter can be determined if the amount of the contained multimers in advance is known and the amount of multimers to be removed by the prefilter to be used is known.

The prefilter may include a monolayer membrane or a multi-layer membrane including two layers or three layers. In the case where the prefilter includes the multi-layer membrane, respective layers may have the same pore size or different pore sizes. For example, the pore sizes of all the three layers may be 0.1 μm.

The prefilter may be sterilized by steam before use. The pressure in filtration of the protein-containing liquid by the prefilter is, for example, 25 kPa (0.25 bar) or less. The prefilter may be sterilized by sterilization-in-place. The sterilization-in-place can prevent contamination with bacteria or the like after a purification step such as ultrafiltration or diafiltration, thereby allowing safety of a preparation to be secured. The sterilization-in-place refers to sterilization of the interior of an apparatus without disassembling of the apparatus.

The particulate substances and the trimers or higher multimers of proteins included in the protein-containing liquid are partially removed by filtration by the prefilter, according to both size exclusion and hydrophobic interaction. The size exclusion in the present disclosure means that the particulate substances having a larger particle size than the filter pore size are captured with the filter and thus removed from the protein-containing liquid. The multimers which are the trimers or the higher multimers and which have a diameter of less than 100 nm are removed from the protein-containing liquid by the prefilter including the hydrophobic resin. The viruses having a size of 50 nm or less, included in the protein-containing liquid, generally penetrates through the prefilter. The viscosity of the protein-containing liquid filtered by the prefilter may be lower than the viscosity of the protein-containing liquid before filtration by the prefilter, in some cases.

Filtration of the protein-containing liquid by the prefilter may be performed after ultrafiltration (UF), diafiltration (DF), or tangent flow (cross-flow) filtration.

As illustrated in FIG. 1, the virus removal membrane 10 for filtration of the protein-containing liquid filtered by the prefilter has a primary surface 1 to which the protein-containing liquid is applied, and a secondary surface 2 from which a liquid that permeates through the virus removal membrane 10 is flowed.

Figure 2:
FIG. 2 is a schematic view of a virus capture portion in a virus removal membrane having a hollow fiber membrane shape, according to Reference Example of the present invention.
Figure 3:
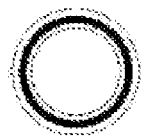
FIG. 3 is a schematic view of a virus capture portion in a virus removal membrane having a hollow fiber membrane shape, according to an embodiment of the present invention.

The virus removal membrane 10 has a virus capture portion, where the viruses are captured, in the cross section thereof. The amount of the viruses captured on the virus capture portion in the cross section is preferably uniform regardless of a point on a filtration surface (primary surface 1) which the solution enters. The reason for this is because, if the amount of the viruses captured on the virus removal membrane is ununiform depending on a point on the filtration surface, the solution is concentrated at certain point on the filtration surface to partially increase the amount of the viruses to be loaded at the point and thus there is a possibility that the viruses are leaked from the point if a large volume filtration is conducted under a high pressure condition. In the case where the virus removal membrane 10 has a hollow fiber membrane shape, the amount of the viruses captured on the virus capture portion is not ununiform as illustrated in FIG. 2, but preferably uniform as illustrated in FIG. 3, in the periphery direction.

Furthermore, in the virus removal membrane 10, the thickness of the virus capture portion is preferably uniform in the virus capture portion. In the case where the virus removal membrane 10 has a hollow fiber membrane shape, the thickness of the virus capture portion is preferably uniform in the periphery direction. In the case where the thickness of the virus capture portion is uniform, the solution can be uniformly spread in the periphery direction to result in reduction in virus leakage.

Here, it may be difficult to visually detect the viruses captured by the virus removal membrane 10. On the contrary, a gold colloid does not allow light to transmit even though it has a diameter comparable with a size of a virus, and therefore it is visually detected easily. Therefore, characteristics of the virus removal membrane 10 can be evaluated by, for example, filtering a gold colloid-containing solution by the virus removal membrane 10, and thereafter measuring the relative brightness of a gold colloid capture portion, where gold colloids are captured by the virus removal membrane 10, in the cross section of the virus removal membrane 10.

With respect to the virus removal membrane 10, when a solution containing gold colloids having a diameter of 20 nm is applied through the primary surface 1 to the virus removal membrane 10 to allow the virus removal membrane 10 to capture the gold colloids for measurement of brightness in the cross section of the virus removal membrane 10, the value obtained by dividing the standard deviation of the value of the area of the spectrum of variation in the brightness by the average of the value of the area of the spectrum of variation in the brightness is 0.01 or more and 1.50 or less. The value expresses the variation coefficient of the amount of the captured gold colloids in the virus removal membrane 10, and a smaller value expresses higher uniformity of the amount of the captured gold colloids on the gold colloid capture portion in the virus removal membrane 10.

In the virus removal membrane 10, the value indicating the variation coefficient is 0.01 or more and 1.50 or less, 0.01 or more and 1.20 or less, 0.01 or more and 1.00 or less, 0.01 or more and 0.90 or less, or 0.01 or more and 0.80 or less. The measurement limit of the variation coefficient is less than 0.01. A variation coefficient of more than 1.50 may cause the solution to be concentrated at at least certain one point in the periphery direction of the membrane to thereby result in virus leakage.

If the variation coefficient is 0.01 or more and 1.50 or less, it can allow viruses to be uniformly captured on the virus capture portion of the membrane (in the periphery direction with respect to a hollow fiber membrane), and allow high virus removal capability to be maintained even in the case of an increase in the total amount of viruses to be loaded to the virus removal membrane (the amount of viruses to be spiked to a protein preparation, or the total amount thereof to be filtered off).

The variation coefficient is measured by, for example, the following method. A piece is cut out from the virus removal membrane applied to filtration of the gold colloid solution, and the brightness profile at each of a plurality of points in a part dyed by the gold colloids in the cross section of the piece is measured by an optical microscope. The gold colloids absorb light and therefore variation in the brightness depends on the amount of the gold colloids to be captured. Herein, a background noise may be, if necessary, removed from the brightness profile. Thereafter, a graph with the thickness represented on the horizontal axis and variation in the brightness represented on the vertical axis is created, and the area of the spectrum of variation in the brightness presented on the graph is calculated. Furthermore, the value obtained by dividing the standard deviation of the area of the spectrum of variation in the brightness at the plurality of points by the average of the area of the spectrum of variation in the brightness at the plurality of points is calculated as the value indicating the variation coefficient of the amount of the captured gold colloids on the gold colloid capture portion in the virus removal membrane 10.

The thickness of a portion (dense layer), where the gold colloids having the diameter of 20 nm or more and 30 nm or less are captured, in the cross section of the virus removal membrane 10 in a wet state is 10 μm or more and 30 μm or less, 10 μm or more and 29 μm or less, 10 μm or more and 28 μm or less, 10 μm or more and 20 μm or less, 11 μm or more and 20 μm or less, or 12 μm or more and 20 μm or less. If a thickness of the portion where the gold colloids having the diameter of 20 nm or more and 30 nm or less are captured is more than 30 μm, it indicates that a pore having a large pore size, through which the gold colloids having the diameter of 20 nm or more and 30 nm or less can pass, is present in a large number, and that the pore size distribution is thus broad. Therefore, the possibility of virus leakage is increased at a low filtration pressure (flow velocity) and/or in Stop and start or Post-wash including pressure release. On the other hand, when a thickness of the portion where the gold colloids having the diameter of 20 nm or more and 30 nm or less are captured is less than 10 μm, it indicates that a pore through which the gold colloids having the diameter of 20 nm or more and 30 nm or less can pass is present in a small number, and that the pore size distribution is thus narrow. Therefore, clogging of proteins and the like may occur in a narrow region to thereby increase a reduction in filtration rate during filtration, resulting in a reduction in final throughput, and thus such a thickness is not preferable.

The thickness of the portion where the gold colloids having the diameter of 20 nm or more and 30 nm or less are captured is acquired by, for example, the following method. A piece is cut out from the virus removal membrane applied to filtration of each of respective solutions of the gold colloids having the diameters of 20 nm and 30 nm. The brightness profile at each of a plurality of points in a part dyed by the gold colloids in the cross section of the piece is measured by an optical microscope. Herein, first distance "a" from the primary surface 1 of the virus removal membrane 10 to a part on the gold colloid capture portion where is closest to the primary surface is measured in the thickness direction. In addition, second distance "b" from the primary surface 1 of the virus removal membrane 10 to a part on the gold colloid capture portion where is closest to the secondary surface 2 is measured in the thickness direction.

Next, value "A" (=a/c (expressed in percentage)) obtained by dividing first distance "a" by thickness "c" of the wet virus removal membrane and expressed in percentage is calculated at each of the plurality of points, and the average of value "A" at the plurality of points is calculated as a first attainment level. In addition, value "B" (=b/c (expressed in percentage)) obtained by dividing second distance "b" by thickness "c" of the wet virus removal membrane and expressed in percentage is calculated at each of the plurality of points, and the average of value "B" at the plurality of points is calculated as a second attainment level.

Furthermore, as represented by the following equation (2), the value obtained by multiplying the difference between average value $B_{20}$ of the second attainment level in the virus removal membrane applied to a filtration of the gold colloids having the diameter of 20 nm and average value $A_{30}$ of the first attainment level in the virus removal membrane applied to a filtration of the gold colloids having the diameter of 30 nm by average value $C_{AVE}$ of average value $C_{20}$ of the thickness of the wet virus removal membrane applied to a filtration of the gold colloids having the diameter of 20 nm and average $C_{30}$ of the thickness of the wet virus removal membrane applied to a filtration of the gold colloids having the diameter of 30 nm is calculated as thickness "T" of the portion, where the gold colloids having the diameter of 20 nm or more and 30 nm or less are captured, in the cross section of the virus removal membrane 10 when the gold colloids having the diameter of 20 nm and the gold colloids having the diameter of 30 nm are flowed. Thickness "T" of the gold colloid capture portion is also expressed as thickness "T" of the dense layer of the virus removal membrane.

$$T=(B_{20}-A_{30}) \times C_{AVE} \qquad (2)$$

In the above method, the portion where the gold colloids having the diameter of 20 nm or more and 30 nm or less are captured is determined as the thickness of a region between the first attainment position in the virus removal membrane applied to the filtration of the gold colloids having the diameter of 30 nm and the second attainment position in the virus removal membrane applied to the filtration of the gold colloids having the diameter of 20 nm, and it is confirmed that the gold colloids having the diameter of 20 nm or more and 30 nm or less, except for the margin of error, are captured within the region.

The thickness of a portion (densest layer), where the gold colloids having the diameter of 15 nm are captured, in the cross section of the virus removal membrane 10 in a wet state is desirably 2 μm or more and 10 μm or less, more preferably 3 μm or more and 10 μm or less. When a thickness of such a gold colloid capture portion is more than 10 μm, efficiency of filtration of not only a gold colloid-containing solution, but also a virus-containing solution tends to be reduced. A thickness of less than 2 μm is not preferable because an increase in the total amount of viruses to be loaded to the virus removal membrane (the amount of viruses to be spiked to a protein preparation, or the total amount thereof to be filtered off) and variation in the filtration pressure along with operating may cause virus leakage.

The thickness of the portion where the gold colloids having the diameter of 15 nm are captured is acquired by, for example, the following method. A piece is cut out from the virus removal membrane applied to filtration of a solution of the gold colloid having the diameter of 15 nm. The brightness profile at each of a plurality of points in the part dyed by the gold colloids in the cross section of the piece is measured by an optical microscope. Herein, first distance "d" from the primary surface 1 of the virus removal membrane 10 to a part on the gold colloid capture portion where is closest to the primary surface is measured in the thickness direction. In addition, second distance "e" from the primary surface 1 of the virus removal membrane 10 to a part on the gold colloid capture portion where is closest to the secondary surface 2 is measured in the thickness direction.

Next, value "D" (=d/f (expressed in percentage)) obtained by dividing first distance "d" by thickness "f" of the wet virus removal membrane and expressed in percentage is calculated at each of the plurality of points, and the average of value "D" at the plurality of points is calculated as a first attainment level. In addition, value "E" (=e/f (expressed in percentage)) obtained by dividing second distance "e" by thickness "f" of the wet virus removal membrane and expressed in percentage is calculated at each of the plurality of points, and the average of value "E" at the plurality of points is calculated as a second attainment level.

Furthermore, as represented by the following equation (3), the value obtained by multiplying the difference between average "E" of the second attainment level and average "D" of the first attainment level by average "F" of the thickness of the virus removal membrane subjected to filtration, in a wet state, is calculated as thickness "T" of the portion, where the gold colloids having the diameter of 15 nm are captured, in the cross section of the virus removal membrane 10 when the gold colloids having the diameter of 15 nm is flowed. Thickness "T" of the portion, where the gold colloids having the diameter of 15 nm are captured, is also expressed as thickness "T" of the densest layer of the virus removal membrane.

$$T=(E-D) \times F \qquad (3)$$

In the case where a solution containing the gold colloids having the diameter of 30 nm is filtered by the virus removal membrane 10, the portion where the gold colloids having the diameter of 30 nm are captured in the cross section of the virus removal membrane 10 in a wet state is located at a place corresponding to, for example, 15% or more and 60% or less, or 20% or more and 55% or less of the membrane thickness from the primary surface 1 in measurement with an optical microscope. A value of less than 15% of the membrane thickness causes viruses and impurities to be captured at a position closer to the primary surface of the membrane and clogging may more occur. A value of more than 60% of the membrane thickness causes the intended viruses to be captured at a position closer to the secondary surface of the membrane and thus the viruses cannot be sometimes captured. Herein, even in the case where a small amount of the gold colloids having the diameter of 30 nm is captured in a region of less than 15% or more than 60% of the membrane thickness from the primary surface 1, a case where the absolute value of the spectrum of variation in the brightness, determined by subtracting the brightness profile measured from a constant (255) in measurement with an optical microscope, is 10% or less relative to the maximum of the absolute value of the spectrum can be regarded as being within the margin of error with respect of capturing of the gold colloids in the region in terms of virus removal ability of the virus removal membrane, and therefore the portion where the gold colloids having the diameter of 30 nm are captured can be regarded as being located at a place corresponding to 15% or more and 60% or less of the membrane thickness from the primary surface 1.

In the case where a solution containing the gold colloids having the diameter of 20 nm is filtered by the virus removal membrane 10, a portion where the gold colloids having the diameter of 20 nm are captured in the cross section of the virus removal membrane 10 in a wet state is located at a place corresponding to, for example, 25% or more and 85% or less, or 30% or more and 85% or less of the membrane thickness from the primary surface 1 in measurement with an optical microscope. A value of less than 25% of the membrane thickness causes viruses and impurities to be captured at a position closer to the primary surface of the membrane and clogging may more occur. A value of more than 85% of the membrane thickness causes the intended viruses to be captured at a position closer to the secondary surface of the membrane and thus the viruses cannot be sometimes captured. Herein, even when the gold colloids are observed in a region of less than 25% or more than 85% of the membrane thickness from the primary surface 1 as in the case of the gold colloids having the diameter of 30 nm, a case where the absolute value of the spectrum of variation in the brightness, determined by subtracting the brightness profile measured from a constant (255) in measurement with an optical microscope, is 10% or less relative to the maximum of the absolute value of the spectrum can be regarded as being within the margin of error.

In the case where a solution containing the gold colloids having the diameter of 15 nm is filtered by the virus removal membrane 10, a portion where the gold colloids having the diameter of 15 nm are captured in the cross section of the virus removal membrane 10 in a wet state is located at a place corresponding to, for example, 60% or more and 100% or less, or 65% or more and 100% or less of the membrane thickness from the primary surface 1 in measurement with an optical microscope. A value of less than 60% of the membrane thickness causes viruses and impurities to be captured at a position closer to the primary surface of the membrane and clogging may more occur. Herein, even when the gold colloids are observed in a region of less than 60% of the membrane thickness from the primary surface 1 as in the cases of respective gold colloids having diameters of 30 nm and 20 nm, a case where the absolute value of the spectrum of variation in the brightness, determined by subtracting the brightness profile measured from a constant (255) in measurement with an optical microscope, is 10% or less relative to the maximum of the absolute value of the spectrum can be regarded as being within the margin of error.

The capture position of each of the respective gold colloids having the diameters of 30 nm, 20 nm and 15 nm is consistently measured with respect to the gold colloids captured by the membrane. Accordingly, the gold colloids that are not captured by the membrane and that permeate through the membrane are not measured. In other words, the capture position of every gold colloid allowed to permeate through the membrane is not measured, but the capture position of the gold colloids captured by the membrane, on the membrane, is measured.

In the case where a solution containing the gold colloids having the diameter of 10 nm is filtered by the virus removal membrane 10, almost no gold colloid having the diameter of 10 nm is captured in the cross section of the virus removal membrane 10. This can be confirmed from the following: the spectrum of the brightness cannot be significantly detected in observation using an optical microscope (Biozero, BZ 8100, manufactured by Keyence Corporation). This can also be confirmed from a reduction in a logarithmic removal rate (LRV) described later. Herein, no gold colloid having the diameter of 10 nm being captured indicates that a useful protein having a diameter of about 10 nm, such as IgG, can achieve high permeability.

The synthetic polymer as the material of the virus removal membrane is preferably a thermoplastic crystalline resin, which is easy of processing such as compression, extrusion, injection, inflation, and blow moldings, and is excellent in pressure resistance in filtration. In particular, a polyolefin resin and a fluororesin are preferable because of having heat resistance and molding processability in a well-balanced manner, and in particular, a polyvinylidene fluoride resin is preferable.

Herein, such a hydrophobic thermoplastic crystal resin causes adsorption of proteins and the like, and contamination, clogging and the like of the membrane to easily occur, resulting in a rapid reduction in filtration rate. Therefore, in the case where a hydrophobic resin is used as the material of the virus removal membrane, hydrophilicity is imparted to the membrane in order to prevent occlusion due to adsorption of proteins and the like. In order to impart hydrophilicity, the membrane preferably has hydrophilic graft chains by a graft polymerization method.

Figure 4:
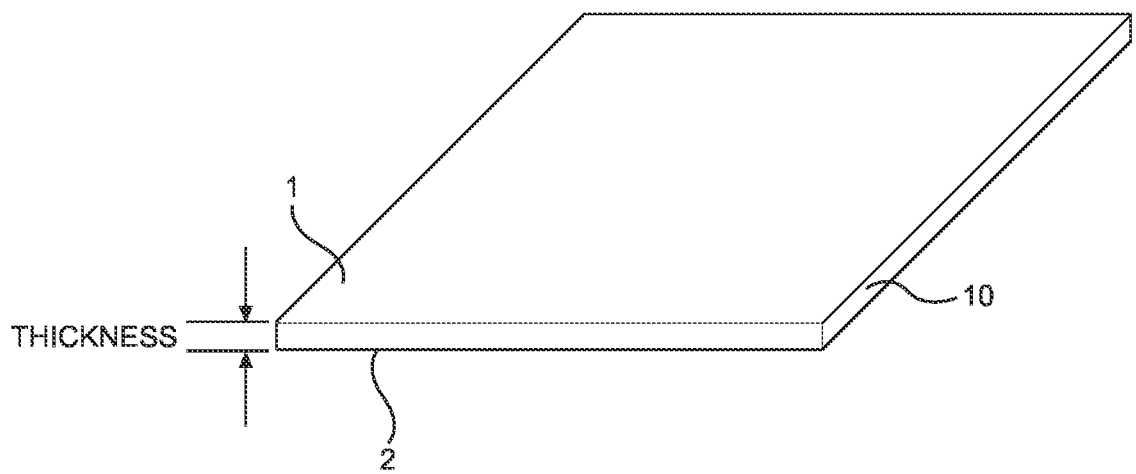
FIG. 4 is a schematic view of a virus removal membrane having a flat membrane shape, according to an embodiment of the present invention.

The virus removal membrane 10 has, for example, a hollow fiber membrane shape. Alternatively, the virus removal membrane 10 may have a flat membrane shape as illustrated in FIG. 4. The membrane is preferably a hollow fiber membrane, because it can be packed in a container to make a compact filter while having a large membrane area.

The thickness of the virus removal membrane 10 shown in FIG. 1 is, for example, 40.0 μm or more and 60.0 μm or less, more preferably 42.0 μm or more and 55.0 μm or less, in a dry state. A membrane thickness of less than 40.0 μm may result in a reduction in strength of the membrane to cause the membrane not to withstand the filtration pressure, and a thickness of more than 60.0 μm may result in a reduction in filtration rate.

The pore size of the pore is decreased and is then constant, from the primary surface towards the secondary surface in the cross section of the virus removal membrane 10, and the virus removal membrane 10 preferably has a densest layer in the vicinity of the outermost layer close to the secondary surface. As the virus removal membrane 10 has the densest layer in the vicinity of the outermost layer, virus leakage at a low filtration pressure (flow velocity) and/or in filtration in a Stop & start or Post-wash system can be reduced more.

The logarithmic removal rate (LRV: Logarithmic Reduction Value) of viruses by the virus removal membrane 10 is preferably, for example, 4.00 or more because the viruses are sufficiently removed by membrane filtration, and the logarithmic removal rate is more preferably 4.50 or more, 5.00 or more, or 6.00 or more. A logarithmic removal rate of viruses of 6.00 or more is considered to allow the viruses to be removed, resulting in almost no virus leakage.

The virus removal membrane 10 has a logarithmic removal rate (LRV) of the gold colloids having the diameter of 30 nm, of, for example, 1.00 or more, preferably 1.20 or more. The virus removal membrane 10 has a logarithmic removal rate of the gold colloids having the diameter of 20 nm, of, for example, 1.00 or more, preferably 1.20 or more. The virus removal membrane 10 has a logarithmic removal rate of the gold colloids having the diameter of 15 nm, of, for example, 0.10 or more, preferably 0.20 or more. The virus removal membrane 10 has a logarithmic removal rate of the gold colloids having the diameter of 10 nm, of, for example, less than 0.10.

The bubble point measured in the virus removal membrane 10 is, for example, 1.30 MPa or more and 1.80 MPa or less, more preferably 1.40 MPa or more and 1.80 MPa or less, 1.45 MPa or more and 1.80 MPa or less, or 1.50 MPa or more and 1.80 MPa or less. Characteristics of the virus removal membrane can also be expressed as the ratio of the bubble point (MPa) to the surface tension (N/m) of a solvent used for measurement. In the case where hydrofluoroether, which has a surface tension of 13.6 mN/m, is used as a test liquid for immersion of the membrane, the ratio of the bubble point to the surface tension is 96 or more and 133 or less, more preferably 103 or more and 133 or less, 106 or more and 133 or less, or 110 or more and 133 or less.

A bubble point of 1.30 MPa or less indicates that pores having a large size are present, and is not preferable because deterioration in virus removal property is observed under conditions including (1) a step of reducing the pressure level, (2) a step of temporarily interrupting filtration to perform repressurizing (Stop & start), or (3) a step of temporarily interrupting filtration after filtration of a preparation, for washing with a Buffer (Post-wash), in particular, in use of a virus removal membrane. A bubble point of 1.80

MPa or more indicates that pores having a small pore size are present, and is not preferable because pure water permeation rate decreases.

The pure water permeation rate measured in the virus removal membrane 10 is 30 L/m$^2$/hrs/0.1 MPa, or more and 80 L/m$^2$/hrs/0.1 MPa, or less, 30 L/m$^2$/hrs/0.1 MPa, or more and 60 L/m$^2$/hrs/0.1 MPa, or less, or 30 L/m$^2$/hrs/0.1 MPa, or more and 55 L/m$^2$/hrs/0.1 MPa, or less.

The virus removal membrane may be sterilized by steam before use. The protein-containing liquid subjected to prefiltration by the prefilter is filtered by the virus removal membrane, and thus the viruses included in the protein-containing liquid are removed. The particulate substances and the multimers of proteins remaining in the protein-containing liquid are also removed.

The filtration method may include no other step between the prefiltration step by the prefilter and the virus removal step. That is, respective steps may be performed in a batch manner. The prefiltration step and the virus removal step may also be performed in a successive manner. In the case where the prefiltration step and the virus removal step are performed in a successive manner, generation of multimers of proteins over time tends to be suppressed to result in a more enhancement in filtration efficiency by the virus removal membrane.

The virus removal membrane, having characteristics described above, is manufactured by, for example, a method described below.

The thermoplastic resin for use as the material of the virus removal membrane is, for example, a thermoplastic resin having crystallinity, for use in usual compression, extrusion, injection, inflation, and blow moldings. For example, polyolefin resins such as a polyethylene resin, a polypropylene resin and a poly-4-methyl-1-pentene resin, polyester resins such as a polyethylene terephthalate resin, a polybutylene terephthalate resin, a polyethylene terenaphthalate resin, a polybutylene naphthalate resin and a polycyclohexylenedimethylene terephthalate resin, polyamide resins such as nylon 6, nylon 66, nylon 610, nylon 612, nylon 11, nylon 12 and nylon 46, fluororesins such as a polyvinylidene fluoride resin, an ethylene/tetrafluoroethylene resin and a polychlorotrifluoroethylene resin, a polyphenylene ether resin, and a polyacetal resin can be used.

Among the above thermoplastic resins, a polyolefin resin and a fluororesin are preferable because of having heat resistance and molding processability in a well-balanced manner, and in particular, a polyvinylidene fluoride resin is preferable. The polyvinylidene fluoride resin here refers to a fluororesin that has a vinylidene fluoride unit in the base backbone and is a resin commonly referred to as an abbreviation "PVDF". As such a polyvinylidene fluoride resin, a homopolymer of vinylidene fluoride (VDF), or a copolymer of one or more monomers selected from the monomer group consisting of hexafluoropropylene (HFP), pentafluoropropylene (PFP), tetrafluoroethylene (TFE), chlorotrifluoroethylene (CTFE) and perfluoromethyl vinyl ether (PFMVE) with vinylidene fluoride (VDF) can be used. The homopolymer and the copolymer can also be used as a mixture thereof. In the embodiment, it is preferable to use a polyvinylidene fluoride resin including 30% by weight or more and 100% by weight or less of the homopolymer because a microporous membrane is enhanced in crystallinity to have a high strength, and it is further preferable to use only the homopolymer.

The average molecular weight of the thermoplastic resin for use in the embodiment is preferably 50000 or more and 5000000 or less, more preferably 100000 or more and 2000000 or less, further preferably 150000 or more and 1000000 or less. While the average molecular weight refers to a weight average molecular weight obtained by gel permeation chromatography (GPC) measurement, it is generally difficult to perform accurate GPC measurement of a resin having an average molecular weight of more than 1000000, and the viscosity average molecular weight by the viscosity method can be thus adopted as an alternative. A weight average molecular weight of less than 50000 is not preferable because of causing melt tension in melt molding to be decreased to result in deterioration in moldability or a reduction in mechanical strength of the membrane. A weight average molecular weight of more than 5000000 is not preferable because of making uniform melt kneading difficult.

The polymer concentration of the thermoplastic resin for use in the embodiment in a composition including the thermoplastic resin and a plasticizer is preferably 20% by weight or more and 90% by weight or less, more preferably 30% by weight or more and 80% by weight or less, most preferably 35% by weight or more and 70% by weight or less. A polymer concentration of less than 20% by weight causes the following disadvantages: membrane formation ability is deteriorated and a sufficient mechanical strength is not achieved. In addition, the resulting microporous membrane has a large pore size for a membrane for virus removal to cause virus removal capability to be insufficient. A polymer concentration of more than 90% by weight causes the resulting microporous membrane to have a too small pore size and a low porosity, thereby resulting in reduction in filtration rate and not withstanding practical use.

As the plasticizer for use in the embodiment, a non-volatile solvent is used which, when mixed with the thermoplastic resin in the composition for manufacturing a microporous membrane, can form a uniform solution at a temperature not lower than the crystal melting point of the resin. The non-volatile solvent here refers to a solvent having a boiling point of 250.0° C. or higher under the atmospheric pressure. The plasticizer may be generally in the form of a liquid or solid at an ordinary temperature of 20.0° C. A plasticizer of a so-called solid-liquid phase separation system, which has a thermally induced solid-liquid phase separation point at a temperature not lower than an ordinary temperature in cooling of the uniform solution with the thermoplastic resin, is preferably used in terms of manufacturing of a membrane for use in virus removal, which is small in pore size and has a homogeneous dense structure layer. Among plasticizers, some has a thermally induced liquid-liquid phase separation point at a temperature not lower than an ordinary temperature in cooling of the uniform solution with the thermoplastic resin, and in the case where a plasticizer of a liquid-liquid phase separation system is used, the resulting microporous membrane generally tends to have a large pore size. The plasticizer used here may be a single substance or a mixture of a plurality of substances.

In the method for measuring the thermally induced solid-liquid phase separation point, the thermally induced solid-liquid phase separation point can be determined by using a composition including the thermoplastic resin and the plasticizer and having a predetermined concentration, melt kneaded in advance, as a sample, and measuring the exothermic peak temperature of the resin by thermal analysis (DSC). In the method for measuring the crystallization point of the resin, the crystallization point can be determined by using the resin melt kneaded in advance, as a sample, and similarly conducting the thermal analysis.

The plasticizer to be preferably used for manufacturing the membrane for use in virus removal, the membrane being small in pore size and having a homogeneous dense structure layer, includes a plasticizer disclosed in International Publication No. WO 01/28667. That is, such a plasticizer is a plasticizer having a phase separation point depression constant of the composition, defined by the following equation (4), of 0.0° C. or more and 40.0° C. or less, preferably a plasticizer having a phase separation point depression constant of 1.0° C. or more and 35.0° C. or less, further preferably a plasticizer having a phase separation point depression constant of 5.0° C. or more and 30.0° C. or less. A phase separation point depression constant of more than 40.0° C. is not preferable because of resulting in reductions in homogeneity of the pore size and strength.

$$\alpha = 100 \times (Tc_0 - Tc)/(100 - C) \quad (4)$$

wherein, $\alpha$ represents the phase separation temperature depression constant (° C.), $Tc_0$ represents the crystallization temperature (° C.) of the thermoplastic resin, $Tc$ represents the thermally induced solid-liquid phase separation point (° C.) of the composition, and $C$ represents the concentration (% by weight) of the thermoplastic resin in the composition.

For example, in the case where a polyvinylidene fluoride resin is selected as the thermoplastic resin, dicyclohexyl phthalate (DCHP), diamyl phthalate (DAP), triphenyl phosphate (TPP), diphenylcresyl phosphate (CDP), tricresyl phosphate (TCP), and the like are particularly preferable.

In the embodiment, the first method for uniformly dissolving the composition including the thermoplastic resin and the plasticizer is a method including loading the resin into a continuous resin kneading apparatus such as an extruder, and introducing the plasticizer at any ratio while heating and melting the resin, for screw kneading, to provide a uniform solution. The resin to be loaded may be in any form of a powder, a granule and a pellet. In the case where uniform dissolution is achieved by such a method, the plasticizer is preferably in the form of an ordinary temperature liquid. As the extruder, a single screw extruder, a twin different direction screw extruder, a twin same direction screw extruder, and the like can be used.

The second method for uniformly dissolving the composition including the thermoplastic resin and the plasticizer is a method including using a stirring apparatus such as a Henschel mixer to mix the resin and the plasticizer in advance for dispersing, and loading the resulting composition into a continuous resin kneading apparatus such as an extruder for melt kneading, to thereby provide a uniform solution. The composition to be loaded may be in the form of a slurry in the case where the plasticizer is an ordinary temperature liquid, or may be in the form of a powder or a granule in the case where the plasticizer is an ordinary temperature solid.

The third method for uniformly dissolving the composition including the thermoplastic resin and the plasticizer is a method for using a simple resin kneading apparatus such as a brabender or a mill, or a method for conducting melt kneading within another batch type kneading vessel. The method includes a batch-wise step, and has the advantages of simplicity and high flexibility.

In the embodiment, the composition including the thermoplastic resin and the plasticizer is heated to a temperature not lower than the crystal melting point of the thermoplastic resin and uniformly dissolved, then extruded in the form of the flat membrane or the hollow fiber through a discharge port of a T-die, a circular die, an annular spinneret or the like, and then cooled and solidified to mold the membrane (step (a)). In step (a) of molding the membrane by cooling and solidifying, the dense structure layer is formed and the coarse structure layer is also formed with being adjacent to the membrane surface.

In the embodiment, while the composition that includes the thermoplastic resin and the plasticizer and is uniformly heated to dissolve is discharged through the discharge port and taken over as the membrane through an air gap part at a taking-over rate so that the draft ratio defined by the following equation (5) is 1.0 or more and 12.0 or less, one surface of the membrane is brought into contact with a non-volatile liquid at 100.0° C. or higher, which can partially dissolve the thermoplastic resin, and other surface of the membrane is cooled to thereby form the coarse structure layer and the dense structure layer in the membrane.

Draft ratio=(taking-over rate of membrane)/(discharge rate of composition at discharge port) (5)

The draft ratio is preferably 1.5 or more and 9.0 or less, more preferably 1.5 or more and 7.0 or less. A draft ratio of less than 1.0 causes tension not to be applied to the membrane, resulting in deterioration in moldability, and a draft ratio of more than 12.0 causes the membrane to be stretched and it tends to make it difficult to form a coarse structure layer having a sufficient thickness. The discharge rate of the composition at the discharge port, of the equation (5), is given by the following equation (6).

Discharge rate of composition at discharge port= (volume of composition to be discharged per unit time)/(area of discharge port) (6)

A preferable range of the discharge rate is 1 m/min or more and 60 m/min or less, more preferably 3 m/min or more and 40 m/min or less. A discharge rate of less than 1 m/min tends to not only cause productivity to be deteriorated, but also cause the problem of an increase in variation in the amount to be discharged to occur. On the contrary, a discharge rate of more than 60 m/min may cause turbulent flow to occur at the discharge port due to a large amount to be discharged, resulting in an unstable discharge state.

The taking-over rate can be set depending on the discharge rate, and is preferably 1 m/min or more and 200 m/min or less, more preferably 3 m/min or more and 150 m/min or less. A taking-over rate of less than 1 m/min tends to cause productivity and moldability to be deteriorated. A taking-over rate of more than 200 m/min tends to cause the cooling time to be shorter and cause the tension applied to the membrane to be increased, thereby easily resulting in breaking of the membrane.

A preferable method for forming the coarse structure layer is a method including extruding the composition including the thermoplastic resin and the plasticizer in the form of the flat membrane or the hollow fiber membrane through an extrusion port to form an uncured membrane, and bringing one surface of the uncured membrane into contact with a non-volatile liquid which can partially dissolve the thermoplastic resin. In such a case, the non-volatile liquid for contact is diffused in the membrane and the thermoplastic resin is partially dissolved to thereby form the coarse structure layer. The liquid which can partially dissolve the thermoplastic resin is here a liquid that can form a uniform solution in a condition of a temperature of 100.0° C. or higher when mixed in a concentration of 50% by weight with the thermoplastic resin, preferably a liquid that can form a uniform solution at a temperature of 100.0° C. or higher and 250.0° C. or lower, further preferably a liquid that can form a uniform solution at a temperature of 120.0° C. or higher and 200.0° C. or lower. In the case where a liquid that provides uniform dissolution at a temperature of less than 100.0° C. is used as the contact liquid, the composition solution including the thermoplastic resin and the plasticizer is inhibited from being cooled and solidified to thereby result in the following disadvantage: moldability is deteriorated, an excess thick coarse structure layer is made, or the pore size is too large. A liquid that cannot form a uniform solution at a temperature of less than 250.0° C. less dissolves the thermoplastic resin to make it difficult to form a sufficiently thick coarse structure layer. The non-volatile liquid is here a liquid having a boiling point higher than 250.0° C. at 1 atm (101325 Pa).

For example, in the case where a polyvinylidene fluoride resin is selected as the thermoplastic resin, phthalic acid esters, adipic acid esters and sebacic acid esters having an ester chain of 7 or less carbon atoms, phosphoric acid esters and citric acid esters having an ester chain of 8 or less carbon atoms, and the like can be suitably used, and in particular, diheptyl phthalate, dibutyl phthalate, diethyl phthalate, dimethyl phthalate, dibutyl adipate, dibutyl sebacate, tri(2-ethylhexyl) phosphate, tributyl phosphate, tributyl acetylcitrate, and the like can be suitably used.

Exceptionally, a plasticizer having a cyclic structure such as a phenyl group, a cresyl group or a cyclohexyl group in the ester chain, namely, dicyclohexyl phthalate (DCHP), diamyl phthalate (DAP), triphenyl phosphate (TPP), diphenylcresyl phosphate (CDP), tricresyl phosphate (TCP), and the like, however, are not preferable because of low ability thereof to form the coarse structure layer.

The temperature of the contact liquid to be used for introducing the coarse structure layer is 100.0° C. or higher, preferably 120.0° C. or higher, which are not higher than the temperature of the uniform solution of the thermoplastic resin and the plasticizer, and is further preferably 130.0° C. or higher, which is not higher than (the temperature of the uniform solution of the thermoplastic resin and the plasticizer—10.0° C.). A temperature of the contact liquid, of lower than 100.0° C., less dissolves the thermoplastic resin, and thus tends to make it difficult to form a sufficiently thick coarse structure layer. A temperature of the contact liquid, of higher than the temperature of the uniform solution of the thermoplastic resin and the plasticizer, causes moldability to be deteriorated.

Furthermore, in the case of the hollow fiber membrane, transfer of heat may occur in passing of the contact liquid through the annular spinneret, to thereby generate the temperature variation in the annular spinneret, resulting in an ununiform membrane structure in the circumferential direction of the hollow fiber. For example, in the case where the contact liquid at a low temperature is introduced from the lateral of the annular spinneret, the temperature of the annular spinneret is decreased on a part where the contact liquid is introduced, and the pore size of the part of the membrane formed from the composition including the thermoplastic resin and the plasticizer which passes through such a part at a relatively low temperature is decreased to thereby increase the ununiformity of the membrane structure in the circumferential direction. In order to obtain the uniform membrane structure in the circumferential direction of the hollow fiber, it is preferable to achieve a uniform temperature of the spinneret, and in order to achieve this, it is preferable to (1) introduce the contact liquid from the upper portion of the annular spinneret in order to achieve a uniform influence of the temperature of the contact liquid in the circumferential direction of the hollow fiber, and/or (2) decrease the difference between the temperature of the annular spinneret and the temperature of the contact liquid immediately before introduction to the annular spinneret in order to decrease heat transfer between the annular spinneret and the contact liquid. In (2), the difference between the temperature of the annular spinneret and the temperature of the contact liquid immediately before introduction to the annular spinneret is preferably 80.0° C. or lower. A difference in temperature of higher than 80.0° C. may cause an ununiform membrane structure in the circumferential direction to be formed, resulting in virus leakage in an increase in the total amount of viruses to be loaded to the virus removal membrane.

In order to decrease the difference between the temperature of the annular spinneret and the temperature of the contact liquid, various methods such as a method for utilizing temperature modulation in the vicinity of the spinneret and a method for decreasing the temperature of the composition including a plastic resin and the plasticizer can be considered, and a method for controlling the temperature of the contact liquid in introduction of the contact liquid to the spinneret, to a high temperature, is preferable.

In the case where the coarse structure layer is introduced on only one surface of the microporous membrane, a method for cooling other surface corresponding to the dense structure layer can be performed according to a conventional method. That is, the membrane can be cooled with being in contact with a thermal conductor. As the thermal conductor, a metal, water, air or the plasticizer itself can be used. Specifically, a method can be utilized which includes extruding the uniform solution including the thermoplastic resin and the plasticizer in the form of the sheet through the T-die or the like, bringing the sheet into contact with a metallic roll for cooling, to form the dense structure layer, and bringing the membrane surface, which is not brought into contact with the roll, into contact with the non-volatile liquid which can partially dissolve the thermoplastic resin, to thereby form the coarse structure layer. A method can also be utilized which includes extruding the uniform solution of the resin and the plasticizer in the form of the cylinder or hollow fiber through the circular die, the annular spinneret or the like, allowing the liquid, which can partially dissolve the thermoplastic resin, to pass through the inside of the cylinder or hollow fiber, to thereby form the coarse structure layer on the inner surface, and bringing the outside into contact with a cooling medium, such as water, for cooling, to thereby form the dense structure layer.

In order to form the homogeneous dense structure layer small in pore size in the method for manufacturing the microporous membrane according to the embodiment, the cooling rate in cooling and solidifying is preferably sufficiently high. The cooling rate is preferably 50.0° C./min or more, more preferably 100.0° C./min or more and $1.0 \times 10^{5}$° C./min or less, further preferably 200.0° C./min or more and $2.0 \times 10^{4}$° C./min or less. A method for bringing into contact with the metallic cooling roll or water is suitably used as a specific method, and in particular, a method for bringing into contact with water is preferable because of being capable of achieving rapid cooling by evaporation of water.

The temperature of the medium for cooling and solidifying is not generally determined and is preferably low depending on the molecular weight of the polymer. For example, in the case of bringing into contact with water, the temperature of water is 50.0° C. or lower, more preferably 40.0° C. or lower, more preferably 30.0° C. or lower. A lower temperature of the medium for contact tends to result in a higher bubble point of the membrane to be formed, and is thus preferable because a high virus removal property can be maintained even in the case of (1) decreasing the pressure (flow velocity) level, (3) temporarily interrupting filtration to perform repressurizing (Stop & start), or (2) temporarily interrupting filtration after filtration of a preparation, for washing with a Buffer (Post-wash), in particular, in use of the virus removal membrane.

In the manufacturing method according to the embodiment, the composition including the thermoplastic resin and the plasticizer and uniformly heated to dissolve is preferably allowed to pass through the air gap after being discharged through the discharge port and before being cooled and solidified. The surface layer of the polymer solution discharged is cooled and a part of the plasticizer is gasified in the air gap to thereby form the densest layer as the densest layer on the surface layer portion. The length of the air gap is preferably 10 mm or more and 300 mm or less, further preferably 30 mm or more and 200 mm or less.

When the length of the air gap is within the above range, a smaller air gap provides the dense layer larger in thickness and a larger air gap provides the dense layer larger in thickness. As long as the length is within the above range, the membrane having a high virus removal capability and a high filtration efficiency can be manufactured.

Furthermore, in the manufacturing method according to the embodiment, a gas release portion may be provided in the air gap part in order to remove the plasticizer gasified, but it is here necessary to pay attention to the flow of air against the discharged composition. In the case where there is variation in the flow of air touched to the discharged composition, variation in the temperature of the composition may be generated to consequently cause local variation in structure to be generated. For example, in the case where the discharged composition is in the form of the hollow fiber, an opposite portion to the gas release portion is more cooled due to the flow of air in gas release from the lateral of the composition, to thereby easily provide the denser structure, resulting in variation in the structure in the circumferential direction. Accordingly, the gas release portion is preferably provided so as to uniform the flow of air with respect to the discharged composition. Specifically, upward gas release or downward gas release is preferably adopted so that the flow of air is in parallel with the discharged composition.

In the case of lateral gas release, the rate of air to be touched to the composition is preferably 10 m/s or less, preferably 7 m/s, 5 m/s, 3 m/s or less, more preferably 1 m/s or less.

In step (b) of removing a substantial part of the plasticizer from the membrane formed, an extraction solvent is used for removing the plasticizer. The extraction solvent preferably serves as a poor solvent to the thermoplastic resin and a good solvent to the plasticizer, and preferably has a boiling point lower than the melting point of the microporous membrane. Examples of such an extraction solvent include hydrocarbons such as hexane and cyclohexane, halogenated hydrocarbons such as methylene chloride and 1,1,1-trichloroethane, alcohols such as ethanol and isopropanol, ethers such as diethyl ether and tetrahydrofuran, ketones such as acetone and 2-butanone, or water.

In an embodiment, the first method for removing the plasticizer from the membrane is performed by immersing the microporous membrane cut out to a predetermined size in a vessel in which the extraction solvent is accommodated, sufficiently washing the microporous membrane, and then drying off the solvent attached, by air or hot air. Here, it is preferable to repeatedly perform the immersion operation and the washing operation several times because the plasticizer remaining in the microporous membrane is decreased. In addition, it is preferable to hold the end of the microporous membrane in order to inhibit the microporous membrane from being shrunk during a series of immersion, washing and drying off operations.

The second method for removing the plasticizer from the membrane is performed by continuously sending the microporous membrane in a tank filled with the extraction solvent, immersing the microporous membrane in the tank over a time sufficient for removal of the plasticizer, and drying off the solvent attached thereafter. Here, it is preferable for an enhancement in extraction efficiency to apply a known procedure such as a multistage method for dividing the interior of the tank to a multistage to sequentially send the microporous membrane to respective tanks with a difference in concentration, or a counterflow method for feeding the extraction solvent in an opposite direction to the traveling direction of the microporous membrane to provide the concentration gradient. In both the first and second methods, it is important to substantially remove the plasticizer from the microporous membrane. The substantial removal refers to removal of the plasticizer in the microporous membrane to such an extent that function as a separation membrane is not impaired, and the amount of the plasticizer remaining in the microporous membrane is preferably 1% by weight or less, further preferably 100 ppm by mass or less. The amount of the plasticizer remaining in the microporous membrane can be quantitatively determined by gas chromatography, liquid chromatography or the like. In addition, it is further preferable to warm the extraction solvent at a temperature lower than the boiling point of the solvent, preferably a temperature in the range of (boiling point—5.0° C.) or lower because diffusion of the plasticizer and the solvent can be promoted to result in an enhancement in extraction efficiency.

A microporous membrane made of a hydrophobic resin excellent in physical strength is excellent as compared with a microporous membrane made of a hydrophilic resin such as cellulose, from the viewpoint of being capable of withstanding a high filtration pressure, but causes adsorption of proteins and the like, and contamination, clogging and the like of the membrane to easily occur, resulting in a rapid reduction in filtration rate. Therefore, in the case where the microporous membrane made of a hydrophobic resin is used, hydrophilicity is imparted to the membrane in order to prevent occlusion due to adsorption of proteins and the like. In the manufacturing method according to an embodiment, it is preferable to introduce hydrophilic functional groups on the pore surface of the hydrophobic membrane by a graft polymerization method to reduce adsorption property of proteins and the like. The reason for this is because the graft polymerization method can uniformly hydrophilize not only large pores but also small pores and can equally hydrophilize not only the inner surface of the membrane but also the outer surface thereof without variation, as compared with other methods (for example, a method for blending a hydrophilic polymer and a method for coating with a hydrophilic polymer).

In addition, graft polymerization is preferable because hydrophilicity is imparted by chemical bonds and therefore elution in a treatment liquid can less occur as compared with other methods. The graft polymerization method means a reaction in which radicals are generated in the polymer microporous membrane by a procedure such as an ionizing radiation or a chemical reaction and the radicals act as starting points to graft-polymerize monomers in the membrane.

In the embodiment, any procedure can be adopted in order to generate radicals in a polymer microporous membrane, but irradiation with an ionizing radiation is preferably adopted in order to uniformly generate radicals in the entire membrane. With respect to the type of the ionizing radiation, a γ-ray, an electron beam, a β-ray, a neutron ray, and the like can be utilized, and an electron beam or a γ-ray is most preferable in industrial scale implementation. An ionizing radiation is obtained from a radioisotope such as cobalt 60, strontium 90 or cesium 137, or X-ray equipment, an electron beam accelerator, an ultraviolet ray irradiation apparatus or the like.

The exposure dose of an ionizing radiation is preferably 1 kGy or more and 1000 kGy or less, more preferably 2 kGy or more and 500 kGy or less, most preferably 5 kGy or more and 200 kGy or less. An exposure dose of less than 1 kGy does not uniformly generate radicals, and an exposure dose of more than 1000 kGy may cause the membrane strength to be reduced.

A graft polymerization method by irradiation with an ionizing radiation is generally roughly classified to a preirradiation method including generating radicals in a membrane, and then bringing the radicals into contact with a reactive compound, and a coincidence irradiation method including generating radicals in a membrane in the state where the membrane is in contact with a reactive compound. In the embodiment, any method can be applied and a preirradiation method is more preferable because an oligomer is less produced.

In the embodiment, hydrophilic vinyl monomers having one vinyl group as the reactives compound, and if necessary crosslinking agents are used, and brought into contact with the polymer microporous membrane in which radicals are generated. The contact method can be performed in any of a gas phase and a liquid phase, but a method for conducting such contact in a liquid phase that allows graft reactions to uniformly progress is preferable. In order to allow graft reactions to further uniformly progress, in the case where hydrophilic vinyl monomers having one vinyl group are dissolved in a solvent in advance and crosslinking agents are then used, the hydrophilic vinyl monomer and the crosslinking agent are preferably dissolved in a solvent in advance and then brought into contact with the polymer microporous membrane.

As described above, in the method for manufacturing the hydrophilic microporous membrane according to the embodiment, the hydrophilic vinyl monomers having one vinyl group are graft-polymerized in the polymer microporous membrane to impart hydrophilicity onto the pore surface, reducing adsorption of physiologically active substances such as proteins. The hydrophilic vinyl monomer having one vinyl group in the embodiment is a monomer having one vinyl group, which is uniformly dissolved when mixed in a concentration of 1% by vol with pure water at 25.0° C. under the atmospheric pressure. Examples of the hydrophilic vinyl monomer include vinyl monomers having a hydroxyl group or a functional group serving as a precursor thereof, such as hydroxypropyl acrylate and hydroxybutyl acrylate, vinyl monomers having an amide bond, such as vinylpyrrolidone, vinyl monomers having an amino group, such as acrylamide, vinyl monomers having a polyethylene glycol chain, such as polyethylene glycol monoacrylate, vinyl monomers having an anion exchange group, such as triethylammoniumethyl methacrylate, and vinyl monomers having a cation exchange group, such as sulfopropyl methacrylate.

In the embodiment, among the above hydrophilic vinyl monomers, a vinyl monomer having at least one hydroxyl group or a functional group serving as a precursor thereof is preferably used because of resulting in a reduction in receding contact angle of the membrane. More preferably, esters of an acrylic acid or methacrylic acid and a polyhydric alcohol, such as hydroxypropyl acrylate and 2-hydroxyethyl methacrylate, alcohols having an unsaturated bond, such as allyl alcohol, and enol esters such as vinyl acetate and vinyl propionate are used, and most preferably, esters of an acrylic acid or methacrylic acid and a polyhydric alcohol, such as hydroxypropyl acrylate and 2-hydroxyethyl methacrylate are used. A hydrophilic microporous membrane obtained by grafting of hydroxypropyl acrylate can achieve a low receding contact angle and sufficient globulin permeation capability.

The solvent that dissolves the hydrophilic vinyl monomers having one vinyl group and the crosslinking agents used if necessary is not particularly limited as long as it can uniformly dissolve them. Examples of such a solvent include alcohols such as ethanol, isopropanol and t-butyl alcohol, ethers such as diethyl ether and tetrahydrofuran, ketones such as acetone and 2-butanone, water, or mixtures thereof.

In dissolution of the hydrophilic vinyl monomers having one vinyl group and the crosslinking agents used if necessary, the concentration is preferably 3% by vol to 30% by vol, more preferably 3% by vol to 20% by vol, most preferably 3% by vol to 15% by vol. A concentration of 3% by vol or more is preferable because of imparting sufficient hydrophilicity. A concentration of more than 30% by vol is not preferable because a hydrophilization layer may be embedded in the pores and permeation capability tends to be deteriorated.

The amount of the reaction liquid in which the hydrophilic vinyl monomers having one vinyl group and the crosslinking agents used if necessary are dissolved in the solvent to be used in graft polymerization is preferably $1\times10^{-5}$ m$^3$ or more and $1\times10^{-3}$ m$^3$ or less based on 1 g of the polymer microporous membrane. An amount of the reaction liquid of $1\times10^{-5}$ m$^3$ or more and $1\times10^{-3}$ m$^3$ or less provides the membrane sufficient in uniformity. The reaction temperature in graft polymerization is generally 20.0° C. or more and 80.0° C. or less, but not particularly limited.

In the embodiment, a hydrophilization layer suitable for the hydrophobic microporous membrane is introduced to realize high protein permeability. Therefore, the graft ratio thereof to be grafted to the hydrophobic microporous membrane is preferably 3% or more and 50% or less, further preferably 4% or more and 40% or less, most preferably 6% or more and 30% or less. A graft ratio of less than 3% causes hydrophilicity of the membrane to be insufficient, resulting in a rapid reduction in filtration rate along with adsorption of proteins. A graft ratio of more than 50% causes a hydrophilization layer to be embedded in relatively small pores, not resulting in a sufficient filtration rate. The graft ratio here means the value defined by the following equation (7).

$$\text{Graft ratio (\%)}=100\times\{(\text{mass of membrane after grafting}-\text{mass of membrane before grafting})/\text{mass of membrane before grafting}\} \quad (7)$$

Manufacturing Examples 1 to 11

(Manufacturing Virus Removal Membrane)

A powder obtained by stirring and mixing a composition including 49% by weight of a polyvinylidene fluoride resin (KF #1300 manufactured by Kureha Corporation) and 51% by weight of dicyclohexyl phthalate (manufactured by Hokko Chemicals Co., Ltd.) by use of a Henschel mixer at room temperature was loaded through a hopper, melt kneaded at 210.0° C. by use of a twin screw extruder (26 mmφ, L/D=50) to uniformly dissolve, thereafter extruded in the form of a hollow fiber at a discharge rate of 4.2 g/min through a spinneret whose temperature was modulated at 225.0° C. and which included a annular orifice having an inner diameter of 0.8 mm and an outer diameter of 1.05 mm, allowed to pass through an air gap, thereafter cooled and solidified in a water bath whose temperature was modulated at a coagulating bath temperature represented in FIG. 5, and wound up as a skein at a rate of 50 m/min. Here, dibutyl phthalate (manufactured by Daihachi Chemical Industry Co., Ltd.) as a hollowing agent was allowed to flow in the interior of the hollow fiber at a rate of 7.1 g/min. In manufacturing Examples 1 to 11, dibutyl phthalate was introduced from the lateral of the spinneret, and the temperature immediately before introduction to the spinneret and the temperature in discharge from the spinneret were as represented in FIG. 5. The rate of air to be touched to the hollow fiber from the lateral in the air gap was 2.7 m/s. Thereafter, dicyclohexyl phthalate and dibutyl phthalate were removed by extraction with 2-propanol (manufactured by Tokuyama Corporation), 2-propanol attached was replaced with water, and thereafter a heat treatment at 125.0° C. was performed by use of a high pressure steam sterilization apparatus in the state of immersion in water for 4 hours. Thereafter, water attached was replaced with 2-propanol, thereafter vacuum drying at 60.0° C. was performed, and thus a hollow fiber microporous membrane was obtained. The process from extraction to drying was performed while the membrane was fixed in a constant length state in order to prevent shrinkage.

Subsequently, the microporous membrane was subjected to a hydrophilization treatment by a grafting method. A reaction liquid was used which was obtained by dissolving hydroxypropyl acrylate (manufactured by Osaka Organic Chemical Industry Ltd.) in an aqueous 25% by vol 3-butanol (special grade, Junsei Chemical Co., Ltd.) solution so that the concentration was 8% by vol, and subjecting the resultant to nitrogen bubbling for 20 minutes with the temperature being held at 45.0° C. First, the microporous membrane was irradiated with at least 25 kGy of a γ-ray using Co 60 as a radiation source while being cooled by dry ice to −60.0° C. or lower, under a nitrogen atmosphere. The membrane after irradiation was left to still stand under a reduced pressure of 13.4 Pa or less for 15 minutes, and thereafter brought into contact with the reaction liquid at 45.0° C. and left to still stand for 1 hour. Thereafter, the membrane was washed with 2-propanol and subjected to vacuum drying at 60.0° C. to thereby provide a microporous membrane. It was confirmed that water spontaneously penetrated in the pore when the resulting membrane was brought into contact with water. The performance evaluation results of the resulting membrane are represented in FIG. 5.

In Manufacturing Examples 1 to 11, the difference between the inlet temperature and the outlet temperature of the hollowing agent, the air gap length, and the coagulating bath temperature were as represented in FIG. 5. In only Manufacturing Example 6, dibutyl phthalate was introduced through the center of the spinneret. With respect to other membrane manufacturing conditions, the same conditions were adopted in Manufacturing Examples 1 to 11.

(Physical Properties of Virus Removal Membrane)
(1) Outer Diameter and Inner Diameter of Hollow Fiber, and Membrane Thickness The outer diameter and the inner diameter of the hollow fiber microporous membrane were determined by photographing the torn vertical section of the membrane by a stereoscopic microscope (SCOPEMAN 503 manufactured by Moritex Corporation) at 210-magnification. The membrane thickness was calculated as ½ of the difference between the outer diameter and the inner diameter of the hollow fiber. The results are represented in FIG. 5.

(2) Bubble Point

The bubble point (Pa) determined by the bubble point method according to ASTM F316-86 was measured. As the test liquid for immersion of the membrane, hydrofluoroether having a surface tension of 13.6 mN/m (Novec (registered trademark) 7200 manufactured by 3M) was used. The bubble point was defined as a pressure at which, after one hollow fiber membrane having an effective length of 8 cm was installed in a bubble point measurement apparatus, the pressure close to the hollow portion was gradually increased and the flow rate of a membrane permeation gas reached 2.4E-3 L/min. The results are represented in FIG. 5.

(3) Pure Water Permeation Rate

The amount of permeation of pure water by constant pressure dead-end filtration at a temperature of 25.0° C. was measured, and the pure water permeation rate was defined according to the following equation (8) from the membrane area, the filtration pressure (0.1 MPa), and the filtration time. The results are represented in FIG. 5.

$$\text{Pure water permeation rate}(L/m^2/hrs/0.1 \text{ MPa}) = \text{amount of permeation}/(\text{membrane area} \times \text{filtration time}) \quad (8)$$

(Evaluation of Virus Removal Membrane Using Gold Colloids)
(1) Preparation of Gold Colloid Solution Respective solutions including gold colloids having particle sizes of 10, 15, 20, and 30 nm (manufactured by Cytodiagnostics Inc.) were purchased. Next, each of the gold colloid solutions was diluted with distilled water for injection, polyoxyethylene-naphthyl ether (1.59% by vol), and poly(sodium 4-styrenesulfonate) (0.20% by vol) so that the absorbance at the maximum absorption wavelength of the gold colloid of each of the gold colloid solutions, measured by an ultraviolet-visible spectrophotometer UVmini-1240 (manufactured by Shimadzu Corporation), was 0.25.

(2) Filtration of Gold Colloid Solution 40 mL of each of the gold colloid solutions prepared was filtered under a pressure of 196 kPa by the virus removal membrane manufactured in Manufacturing Examples. The filtration surface area of the virus removal membrane was 0.001 $m^2$.

(3) Measurement of Removal Rate of Gold Colloids by Virus Removal Membrane

With respect to each of the gold colloid solutions, absorbance "A" of the gold colloid solution before filtration and absorbance "B" of the filtrate, at the maximum absorption wavelength of the gold colloids, were measured using an ultraviolet-visible spectrophotometer UVmini-1240 (manufactured by Shimadzu Corporation), and the logarithmic removal rate (LRV) of the gold colloids by the virus removal membrane according to Manufacturing Examples, given by the following equation (9), was calculated. The results are represented in FIG. 5.

$$LRV = \log_{10}(A/B) \quad (9)$$

(4) Measurement of Uniformity of Gold Colloid Capture Portion

A piece (thickness: 8 μm) was cut out from the virus removal membrane according to Manufacturing Examples after filtration of each of the gold colloid solutions, and the brightness profile at each of 16 points dyed by the gold colloids in the cross section of the piece was measured by an optical microscope (Biozero, BZ8100, manufactured by Keyence Corporation). Next, the brightness profile measured was subtracted from a constant (255). Thereafter, a graph with the membrane thickness (percentage) represented on the horizontal axis and variation in the brightness represented on the vertical axis was created, and the area of the spectrum of variation in the brightness presented on the graph was calculated. Furthermore, the value obtained by dividing the standard deviation of the area of the spectrum of variation in the brightness at 16 points by the average of the area of the spectrum of variation in the brightness at 16 points was calculated as the value indicating the variation coefficient of the amount of the captured gold colloids, on the gold colloid capture portion in the virus removal membrane according to Manufacturing Examples. The results in flowing of only gold colloids having the diameter of 20 nm are represented in FIG. 5. Accordingly, it was indicated that uniformity of the amount of the captured gold colloids on the gold colloid capture portion of the virus removal membrane according to the Manufacturing Example was high. In addition, among the Manufacturing Examples, as the difference between the inlet temperature and the outlet temperature of the hollowing agent before and after the contact with the uniform solution of the thermoplastic resin and the plasticizer was smaller, uniformity of the amount of the captured gold colloids on the gold colloid capture portion tended to be higher, and when the hollowing agent was loaded through the center of the spinneret, uniformity of the amount of the captured gold colloids on the gold colloid capture portion tended to be higher.

(5) Measurement of Thickness of Gold Colloid Capture Portion

A piece (thickness: 8 μm) was cut out from the virus removal membrane in a wet state with which the respective solutions of the gold colloids having the diameters of 20 and 30 nm were filtered. The brightness profile at each of 16 points dyed by the gold colloids in the cross section of the piece in a wet state was measured by an optical microscope (Biozero, BZ8100, manufactured by Keyence Corporation). Here, first distance "a" from the primary surface of the virus removal membrane to a part on which the gold colloids were captured and where was closest to the primary surface was measured in the thickness direction. In addition, second distance "b" from the primary surface of the virus removal membrane to a part on which the gold colloids were captured and where was closest to the secondary surface was measured in the thickness direction.

Next, value "A" (=a/c (expressed in percentage)) obtained by dividing first distance "a" by thickness "c" of the virus removal membrane in a wet state and expressed in percentage was calculated at each of 16 points, and the average of value "A" at 16 points was calculated as a first attainment level. In addition, value "B" (=b/c (expressed in percentage)) obtained by dividing second distance "b" by thickness "c" of the virus removal membrane in a wet state and expressed in percentage was calculated at each of 16 points, and the average of value "B" at 16 points was calculated as a second attainment level.

Furthermore, as represented by the following equation (10), the value obtained by multiplying the difference between average $B_{20}$ of the second attainment level in the virus removal membrane applied to a filtration of the gold colloids having the diameter of 20 nm and average $A_{30}$ of the first attainment level in the virus removal membrane applied to a filtration of the gold colloids having the diameter of 30 nm by the average $C_{AVE}$ of average $C_{20}$ of the thickness of the virus removal membrane in a wet state applied to a filtration of the gold colloids having the diameter of 20 nm and average $C_{30}$ of the thickness of the virus removal membrane in a wet state applied to a filtration of the gold colloids having the diameter of 30 nm was calculated as thickness "T" of the gold colloid capture portion of the virus removal membrane. Thickness "T" of the gold colloid capture portion is also expressed as thickness "T" of a dense layer of the virus removal membrane. The results are represented in FIG. 5.

$$T=(B_{20}-A_{30})\times C_{AVE} \quad (10)$$

In the above method, at least two virus removal membranes: the virus removal membrane applied to the filtration of the gold colloids having the diameter of 20 nm and the virus removal membrane applied to the filtration of the gold colloids having the diameter of 30 nm; were used to measure the thickness of the dense layer. Only one virus removal membrane, however, can also be used to measure the thickness of the dense layer. In this case, one virus removal membrane is used to filter the gold colloid solution including the gold colloids having both diameters of 20 nm and 30 nm. Alternatively, one virus removal membrane is used to filter the gold colloid solution with the diameter of 20 nm and then filter the gold colloid solution with the diameter of 30 nm.

Thereafter, a piece was cut out from the virus removal membrane with which each of the gold colloid solutions with the diameters of 20 nm and 30 nm was filtered, and the brightness profile at each of 16 points dyed by the gold colloids in the cross section of the piece were measured by an optical microscope (Biozero, BZ8100, manufactured by Keyence Corporation). Herein, first distance "$a_1$" from the primary surface of the virus removal membrane to a part on the gold colloid capture portion where was closest to the primary surface was measured in the thickness direction. In addition, second distance "$b_1$" from the primary surface of the virus removal membrane to a part on the gold colloid capture portion where was closest to the secondary surface was measured in the thickness direction.

Next, value "$A_1$" (=$a_1/c_1$ (expressed in percentage)) obtained by dividing first distance "$a_1$" by thickness "c" of the wet virus removal membrane and expressed in percentage was calculated at each of 16 points, and the average of value "$A_1$" at 16 points was calculated as a first attainment level. In addition, value "$B_1$" (=$b_1/c_1$ (expressed in percentage)) obtained by dividing second distance "$b_1$" by thickness "c" of the wet virus removal membrane and expressed in percentage was calculated at each of 16 points, and the average of value "$B_1$" at 16 points was calculated as a second attainment level.

Furthermore, as represented by the following equation (11), the value obtained by multiplying the difference between average "$B_1$" of the second attainment level in the virus removal membrane and average "$A_1$" of the first attainment level in the virus removal membrane, by average "C" of the thickness of the wet virus removal membrane was calculated as thickness "T" of the gold colloid capture portion of the virus removal membrane. It was confirmed that no large difference occurred between thickness "T" calculated by the equation (10) and thickness "T" calculated by the equation (11).

$$T=(B_1-A_1)\times C \quad (11)$$

(6) Measurement of Thickness of Densest Layer

A piece (thickness: 8 μm) was cut out from the virus removal membrane in a wet state with which the solution of the gold colloids having the diameter of 15 nm was filtered. The brightness profile at each of 16 points dyed by the gold colloids in the cross section of the piece in a wet state was measured by an optical microscope (Biozero, BZ8100, manufactured by Keyence Corporation). Here, first distance "d" from the primary surface of the virus removal membrane to a part on which the gold colloids were captured and where was closest to the primary surface was measured in the thickness direction. In addition, second distance "e" from the primary surface of the virus removal membrane to a part on which the gold colloids were captured and where was closest to the secondary surface was measured in the thickness direction.

Next, value "D" (=d/f (expressed in percentage)) obtained by dividing first distance "d" by thickness "f" of the virus removal membrane in a wet state and expressed in percentage was calculated at each of 16 points, and the average of value "D" at 16 points was calculated as a first attainment level. In addition, value "E" (=e/f (expressed in percentage)) obtained by dividing second distance "e" by thickness "f" of the virus removal membrane in a wet state and expressed in percentage was calculated at each of 16 points, and the average of value "E" at 16 points was calculated as a second attainment level.

Furthermore, as represented by the following equation (12), the value obtained by multiplying the difference between average "E" of the second attainment level and average "D" of the first attainment level in the virus removal membrane applied to a filtration of the gold colloids having the diameter of 15 nm, by average "F" of the thickness of the virus removal membrane in a wet state applied to filtration was calculated as thickness "T" of the 15-nm gold colloid capture portion (densest layer) of the virus removal membrane.

$$T = (E - D) \times F \quad (12)$$

(7) Measurement of Particle Size Dependence Property of Gold Colloid Capture Portion of Virus Removal Membrane A piece (thickness: 8 μm) was cut out from the virus removal membrane with which the respective gold colloid solutions with the diameters of 15 nm, 20 nm and 30 nm were filtered. The brightness profile at each of 16 points dyed by the gold colloids in the cross section of the piece was measured by an optical microscope (Biozero, BZ8100, manufactured by Keyence Corporation). Here, first distance "a" from the primary surface of the virus removal membrane to a part on which the gold colloids were captured and where was closest to the primary surface was measured in the thickness direction. In addition, second distance "b" from the primary surface of the virus removal membrane to a part on which the gold colloids were captured and where was closest to the secondary surface was measured in the thickness direction.

Next, value A (%) obtained by dividing first distance "a" by thickness "c" of the wet virus removal membrane and expressed in percentage was calculated at each of 16 points, and the average of value "A" (%) at 16 points was calculated as a first attainment level. In addition, value "B" (%) obtained by dividing second distance "b" by thickness "c" of the wet virus removal membrane and expressed in percentage was calculated at each of 16 points, and the average of value "B2(%)" at 16 points was calculated as a second attainment level. The average of the first attainment level and the average of the second attainment level with respect to each of respective gold colloids having the diameters of 15 nm, 20 nm and 30 nm are represented in FIG. 5. In FIG. 5, numerical values on the left each represent the average of the first attainment level, and numerical values on the right each represent the average of the second attainment level. The capture position of each of respective gold colloids having the diameters of 30 nm, 20 nm and 15 nm was consistently measured with respect to the gold colloids captured by the membrane, and the gold colloids not captured by the membrane were not measured.

(Virus Removal Ability of Virus Removal Membrane)

(1) Preparation of Virus-Containing Protein Solution

Polyclonal antibodies (human IgG) (Venoglobulin-IH, manufactured by Benesis Corporation) were used to provide an antibody solution that was diluted with water for injection (Otsuka Pharmaceutical Co., Ltd.) so as to have an antibody concentration of 10 mg/mL. The salt concentration was adjusted to 0.1 mol/L by use of an aqueous 1 mol/L NaCl solution. Furthermore, the hydrogen-ion exponent (pH) was adjusted to 4.0 by use of 0.1 mol/L HCl or 0.1 mol/L NaOH, to provide a protein solution. To the resulting protein solution was added porcine parvovirus (PPV; Japanese Association of Veterinary Biologics) in a concentration of 1.0% by vol, and well stirred to provide a virus-containing protein solution.

(2-1) Filtration (Normal) of Virus-Containing Protein Solution

The manufactured virus removal membrane, having the membrane area of 0.001 $m^2$, was used at a filtration pressure of 196 kPa to perform dead-end filtration of the virus-containing protein solution until the amount of filtration reached 150 L/$m^2$.

(2-2) Filtration (Capture Capacity) of Virus-Containing Protein Solution

The manufactured virus removal membrane, having the membrane area of 0.001 $m^2$, was used at a filtration pressure of 196 kPa to perform dead-end filtration of the virus-containing protein solution. The filtration pressure was measured by a pressure gauge disposed close to a feed solution vessel. The filtrate was taken by 15 L/$m^2$, and the filtration was performed until the amount of viruses loaded reached at most 14.0 ($Log_{10}(TCID_{50}/m^2)$).

(3) Measurement of Virus Removal Rate

Prepared was PK-13 cell (ATCC No. CRL-6489) obtained from American Type Culture Collection (ATCC) and cultured. In addition, prepared was a mixed liquid of 3% by vol of bovine serum (manufactured by Upstate) heated in a water bath at 56.0° C. for 30 minutes and inactivated, and D-MEM (manufactured by Invitrogen Corporation, high glucose) containing 1% by vol of penicillin/streptomycin (+10000 Units/mL penicillin, +10000 μg/mL streptomycin, manufactured by Invitrogen Corporation). Hereinafter, the mixed liquid is referred to as "3% by vol FBS/D-MEM". Next, the PK-13 cells were diluted with 3% by vol FBS/D-MEM to prepare a diluted cell suspension having a cell concentration of 2.0×$10^5$ (cells/mL). Next, ten 96-well round-bottom cell culture plates (manufactured by Falcon Corporation) were prepared, and the diluted cell suspension was dispensed to all wells by 100 μL.

Each of the filtrate of the virus-containing protein solution, 10-fold, $10^2$-fold, $10^3$-fold, $10^4$-fold and $10^5$-fold diluted solutions of the filtrate, and $10^2$-fold, $10^3$-fold, $10^4$-fold, $10^5$-fold, $10^6$-fold and $10^7$-fold diluted solutions of the virus-containing protein solution not filtered was dispensed to every eight wells of each of the cell culture plates, to which the diluted cell suspension was dispensed, by 100 μL. Thereafter, each of the cell culture plates was placed in an incubator at 37.0° C. in a 5% carbon dioxide atmosphere, and the cells were cultured for 10 days.

The cells cultured for 10 days were subjected to 50% tissue culture infectious dose (TCID50) measurement by use of the erythrocyte adsorption method (see Experimental Study of Viruses, General, edited by National Institute of Infectious Diseases, p. 173) described below. First, preserved chicken blood (manufactured by Nippon Bio-Test Laboratories Inc.) was diluted 5-fold with PBS (−) (manufactured by Nissui Pharmaceutical Co., Ltd.; prepared by the method described in the instruction attached to the product) and then centrifuged at 2500 rpm at 4.0° C. for 5 minutes to precipitate erythrocytes. Thereafter, the supernatant was removed by aspiration, and the resulting erythrocyte-containing precipitate was diluted again 200-fold with the PBS (−).

Next, the PBS (−) diluted solution of the erythrocyte precipitate was dispensed by 100 μL to all wells of the cell culture plates, and left to still stand for two hours. Thereafter, the presence of the adsorption of erythrocytes to the surface of the cellular tissue cultured was visually confirmed, and a well where the adsorption was confirmed was counted as a well with viral infection and a well where the adsorption was not confirmed was counted as a well without viral infection. Furthermore, the degree of viral infection was confirmed every well, to which each of the filtrate of the virus-containing protein solution and the diluted solutions of the filtrate, and the diluted solutions of the virus-containing protein solution not filtered was dispensed, the $\log_{10}$ $(TCID_{50}/mL)$ was calculated as an infectivity titer according to the Reed-Muench method (see Experimental Study of Viruses, General, edited by National Institute of Infectious Diseases, p. 479-480), and the logarithmic removal rate (LRV) of the viruses was calculated using the following equations (13) and (14). The results are represented in FIG. 5.

$$LRV=\log_{10}(C_0/C_F) \quad (13)$$

In the equation, $C_0$ represents the infectivity titer of the virus-containing protein solution not filtered (virus-containing protein solution) before filtration by the virus removal membrane, and $C_F$ represents the infectivity titer of the filtrate after filtration by the virus removal membrane.

LRV of process including pressure release (Stop & Start):

$$LRV=\log_{10}(C_0\times 150/(C_{F100}\times 100+C_{F50}\times 50)) \quad (14)$$

In the equation, $C_0$ represents the infectivity titer of the virus-containing protein solution not filtered (virus-containing protein solution) before filtration by the virus removal membrane, $C_{F100}$ represents the infectivity titer of the filtrate pool after filtration (100 mL/0.001 m$^2$) by the virus removal membrane before pressure release, and $C_{F50}$ represents the infectivity titer of the filtrate pool left to stand for 3 hours in the virus removal membrane after the pressure release and filtered (50 mL/0.001 m$^2$) after repressurized.

(4) Calculation of Maximum Capture Capacity

The maximum capture capacity of the virus removal membrane was calculated from the amount of filtration (=maximum filtration capacity), at which a value more than the detection limit was obtained in measurement of the virus removal rate, by the calculation method according to the following equation (15).

Maximum capture capacity$(\log_{10}(TCID_{50}/m^2))$=infectivity titer of virus-containing protein solution not filtered$(\log_{10}((TCID_{50}/mL)\times$maximum filtration capacity$(L/m^2)\times 1000))$ (15)

A maximum capture capacity of 10.0 raised to the power of 11.5 or more is preferable because the virus removal rate is not reduced even if the amount of viruses to be loaded to the virus removal membrane is increased. Furthermore, a maximum capture capacity of 10.0 raised to the power of 12 or more, 12.5 or more, or 13.0 or more is further preferable.

As represented in FIG. 5, the maximum capture capacity was increased in accordance with increases in uniformity and the dense layer thickness.

(Production of Multimer-Containing Liquid)

A human immunoglobulin preparation (Blood donation Venoglobulin IH 5%, intravenously administered, Japan Blood Products Organization) was used to prepare a solution having a final globulin concentration of 2% and a sodium chloride concentration of 100 mmol/L. The solution had a pH of 4.5. The solution was decreased in pH to 2.5 by an aqueous 1 mol/L sodium chloride solution at room temperature, left to still stand for 1 hour, thereafter increased in pH to 4.5 by an aqueous 1 mol/L sodium hydroxide solution, and left to still stand for 24 hours, thereby partially converting globulins to multimers. In the present Example, particulate substances were generated with a pH treatment in a severe condition, in order to denature proteins. The multimer-containing solution was hereinafter referred to as solution A.

Figure 6:
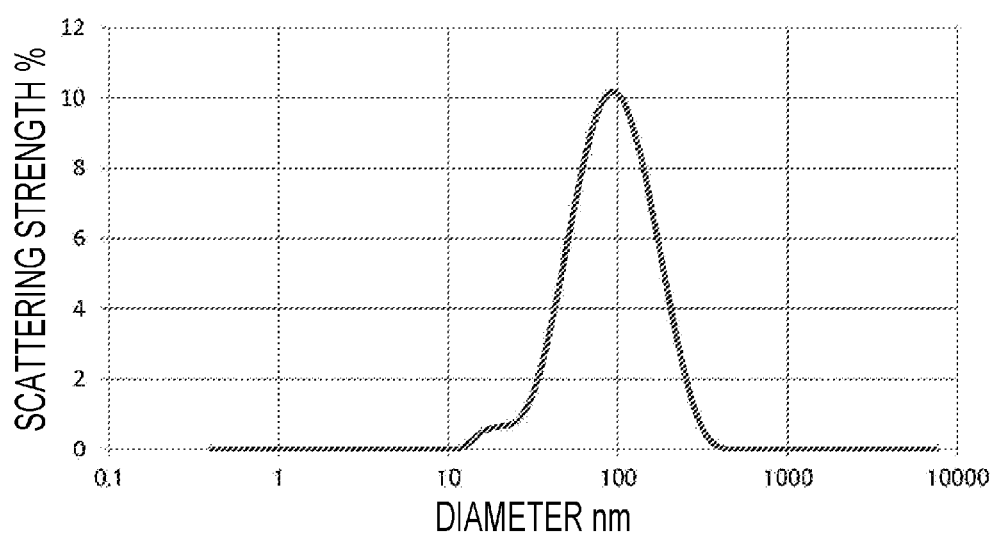
FIG. 6 is a graph representing a particle size distribution of protein particles according to Examples of the present invention.

The average diameter of the particles included in solution A was measured by a dynamic light scattering method, and the average diameter calculated was 74.3 nm. ZetaSizer Nano manufactured by Malvern Panalytical was used for measurement. The results are represented in FIG. 6. The amount of light in measurement (attenuation condition of irradiation light), and the distance from a light source and the total measurement time (cumulative number and measurement time per cumulative number) were set by use of an automatic setting function of the apparatus, and the measurement temperature and the measurement angle were 25.0° C. and 173°, respectively.

Figure 7:
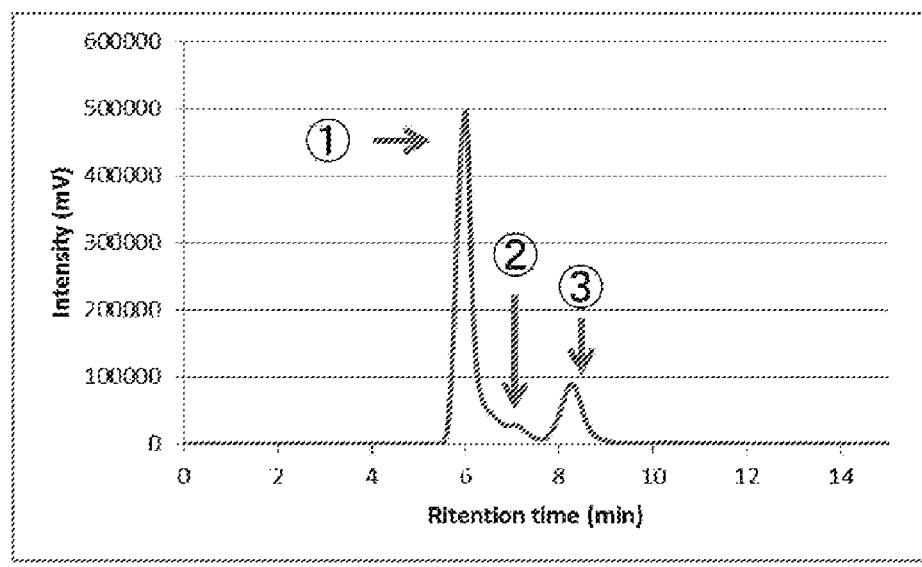
FIG. 7 is a graph of the absorbance in size exclusion chromatography with respect to a multimer-containing liquid according to Examples of the present invention.

Solution A was subjected to size exclusion chromatography analysis, and was found to include 16.5% of monomers, 5.6% of dimers, and 77.8% of trimers or higher multimers based on the relative area ratio calculated from the peak area in the resulting chart. The present Example corresponded to a model experiment where a multimer-containing solution was made and added to a protein solution, and thus measurement of the average diameter of a sample fractionated in size exclusion chromatography analysis was not performed. Such a size exclusion chromatographic method was performed using high-performance liquid chromatograph (Prominence, Shimadzu Corporation) and a column (TSK gel G3000SWXL, Tosoh Corporation, exclusion limit molecular weight: 500,000 Da). The mobile phase included 0.3 mol/L of phosphate buffer having a pH of 6.9, 0.2 mol/L of arginine-HCl, and 0.1 mol/L of NaCl. One example of the measurement results is represented in FIG. 7. Peak (1) in FIG. 7 represents trimers or higher multimers of the globulins, peak (2) represents dimers of the globulins, and peak (3) represents monomers. The respective percentages of the monomers and the multimers were calculated from the peak area in the chromatography chart, thereby providing the relative area ratio. The respective concentrations of the monomers, the multimers and the like in the following Examples are also represented in the same manner by use of the relative area ratio (%). The measurement temperature was 25° C., the measurement time was 20 minutes, and the flow rate was 1.0 mL/min. Such conditions were also applied in the same manner to analysis of the respective percentages of the following monomers and multimers.

Herein, in the following Examples, an experiment was performed after the particles in solution A, having an average diameter of less than 100 nm, and the relative area ratio calculated from the peak area with respect to trimers or higher multimers were confirmed by use of protein solution A where the proteins in the solution mostly included trimers or higher multimers, and a solution to be treated was then prepared so that the content of trimers or higher multimers of proteins having an average diameter of less than 100 nm, in the solution to be treated in each of Examples, was 0.25 g/m$^2$ per 1 m$^2$ of the virus removal membrane.

Example 1

A human immunoglobulin preparation (Blood donation Venoglobulin IH 5%, intravenously administered, Japan Blood Products Organization) was used to prepare 25 mL of a solution having a final globulin concentration of 30 mg/mL, a sodium chloride concentration of 50 mmol/L, and a pH of 5.3, and solution A was added to the solution so that 0.3 mg of multimers was contained.

Figure 8:
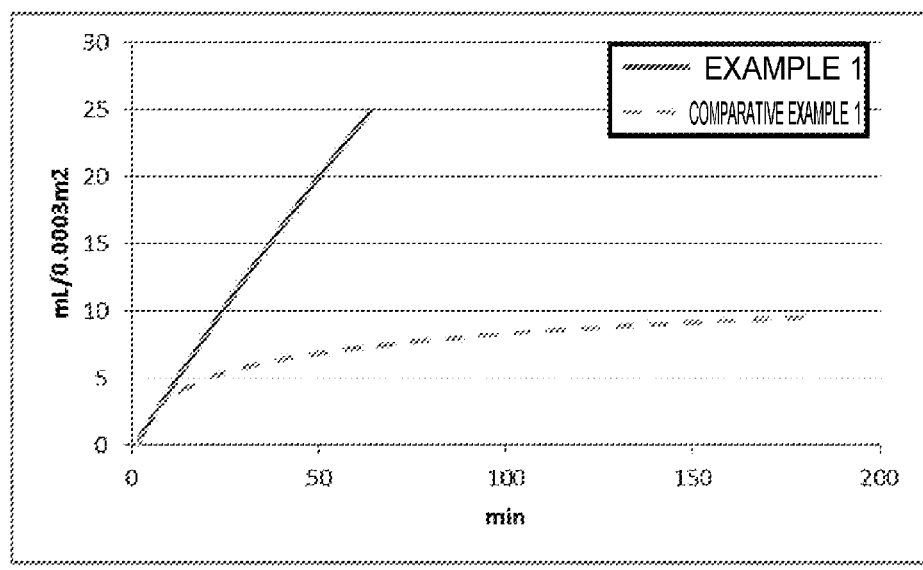
FIG. 8 is a graph representing a temporal change in the total amount of filtrate, by each virus removal membrane according to Example 1 of the present invention and Comparative Example 1.

The total amount of the solution prepared was filtered at a constant pressure of 0.2 bar by Durapore (Merck KGaA) having a membrane area of 10 cm$^2$, including polyvinylidene fluoride (PVDF), and having a pore size of 0.1 μm, prepared as a prefilter. The resulting filtrate was filtered at a constant pressure of 3 bar by a virus removal membrane manufactured in the same conditions as in Manufacturing Example 5, having a membrane area of 3 cm$^2$, and the time taken for filtration of a total amount of 25 mL of the solution prepared was found to be 65 minutes as represented in FIG. 8. The results obtained by conversion of each result of the present test into the total amount to be filtered off per membrane area are represented in FIG. 9.

Comparative Example 1

The same solution as the solution prepared in Example 1 was filtered directly by a virus removal membrane without use of a prefilter, at a constant pressure of 3 bar, and only about 9.6 mL of the solution could be filtered even for 3 hours as represented in FIG. 8. It was expected from such a curve that the time taken for filtration of a total amount of 25 mL of the solution was 4900 hours or more. The multimers here loaded to the virus removal membrane were in an amount of 1 g per 1 m$^2$. The results obtained by conversion of each result of the present test into the total amount to be filtered off per membrane area are represented in FIG. 9.

Example 2

The same method as in Example 1 was performed to prepare 25 mL of a solution having a final globulin concentration of 30 mg/mL, a sodium chloride concentration of 50 mmol/L, and a pH of 5.3, and solution A was added to the solution so that 1.03 mg of multimers was contained.

Figure 10:
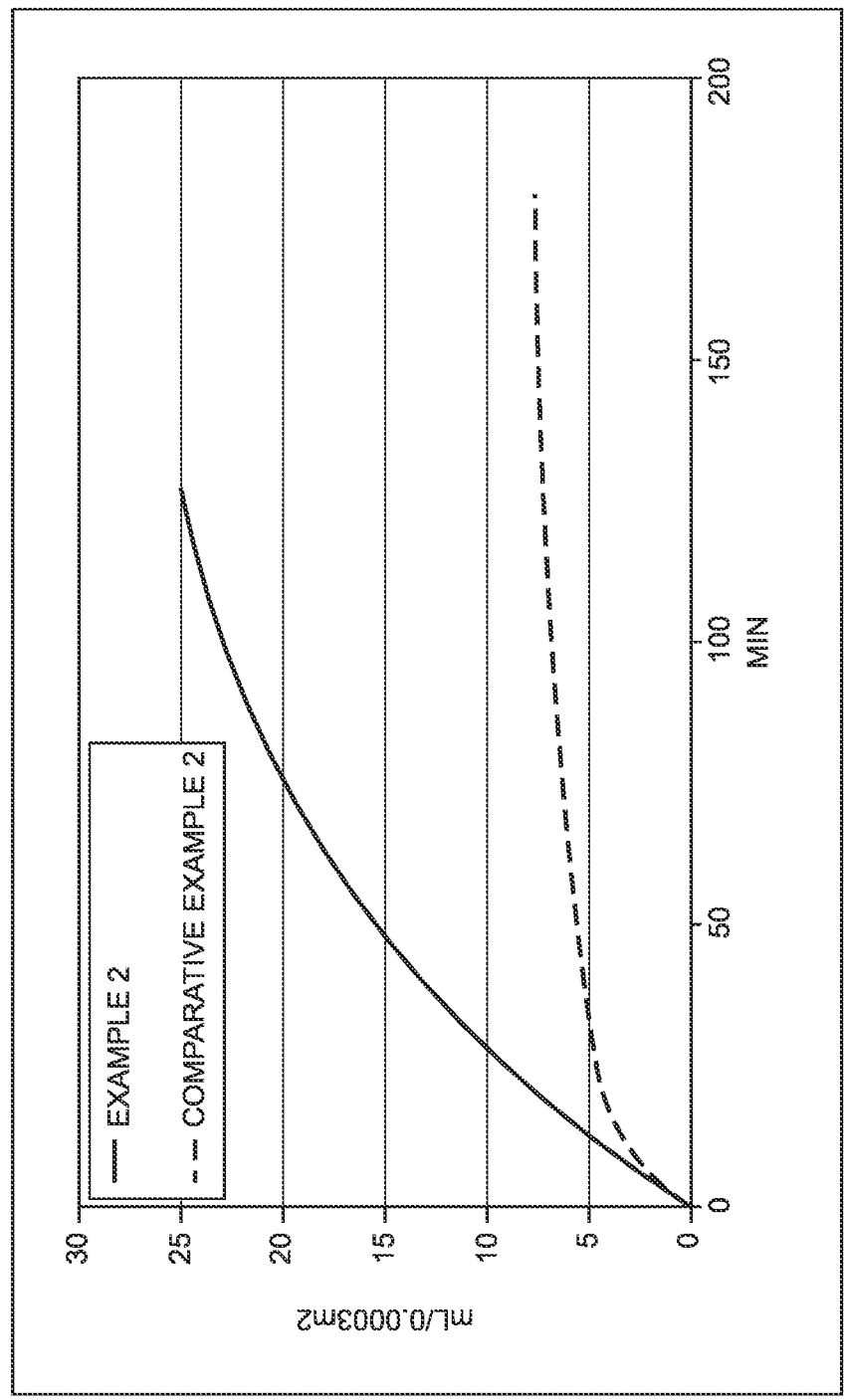
FIG. 10 is a graph representing a temporal change in the total amount of filtrate, by each virus removal membrane according to Example 2 of the present invention and Comparative Example 2.

The prefilter prepared was Virosart Max (Sartorius Stedim Japan K. K.) in which three layers having a membrane area of 5 cm$^2$, including polyamide and having a pore size of 0.1 μm were stacked, and filtration at a constant pressure of 0.2 bar was performed. Two of the prefilters were prepared, and the first filter was again connected to the second filter at a position where 12.5 mL of a liquid to be treated, corresponding to the half the total amount of the liquid, was filtered. The resulting filtrate was filtered at a constant pressure of 3 bar by a virus removal membrane manufactured in the same conditions as in Manufacturing Example 5, having a membrane area of 3 cm$^2$, and the time taken for filtration of a total amount of 25 mL of the solution prepared was 128 minutes as represented in FIG. 10. The results obtained by conversion of each result of the present test into the total amount to be filtered off per membrane area are represented in FIG. 9.

Comparative Example 2

The same solution as the solution prepared in Example 2 was filtered directly by a virus removal membrane without use of a prefilter, at a constant pressure of 3 bar, and only about 7.7 mL of the solution could be filtered even for 3 hours, as represented in FIG. 10. It was expected from such a curve that the time taken for filtration of a total amount of 25 mL of the solution was 150,000 hours or more. The multimers here loaded to the virus removal membrane were in an amount of 3.4 g per 1 m$^2$. The results obtained by conversion of each result of the present test into the total amount to be filtered off per membrane area are represented in FIG. 9.

Example 3

Figure 11:
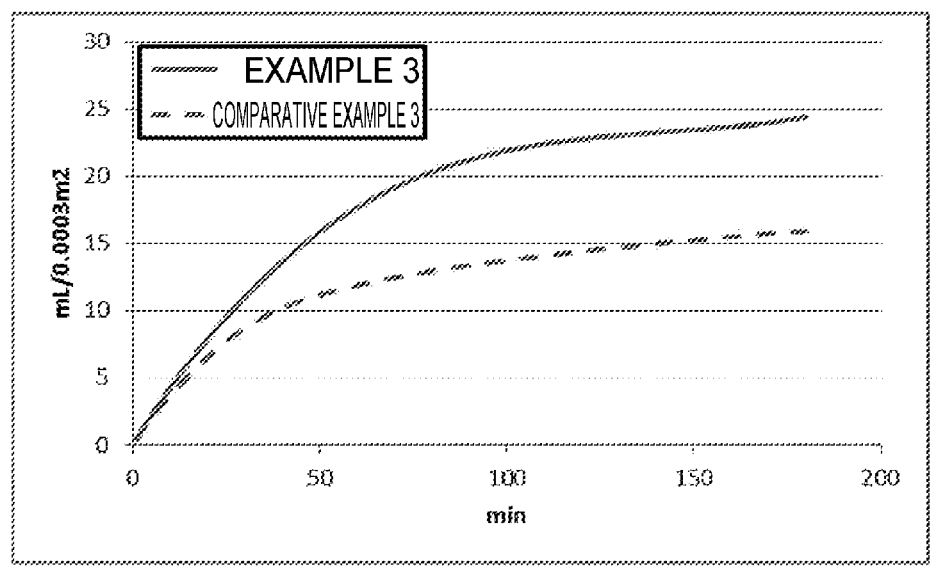
FIG. 11 is a graph representing a temporal change in the total amount of filtrate, by each virus removal membrane according to Example 3 of the present invention and Comparative Example 3.

The same method as in Example 1 was performed to prepare 25 mL of a solution having a final globulin concentration of 30 mg/mL, a sodium chloride concentration of 50 mmol/L, and a pH of 5.3, and solution A was added to the solution so that 0.15 mg of multimers was contained. The prefilter prepared was Supor (Pall Corporation) having a membrane area of 5.8 cm$^2$, including polyether sulfone and having a pore size of 0.2 μm, and filtration at a constant pressure of 0.2 bar was performed. Two of the prefilters were prepared, and the first filter was again connected to the second filter at a position where 12.5 mL of a liquid to be treated, corresponding to the half the total amount of the liquid, was filtered. The resulting filtrate was filtered at a constant pressure of 3 bar by a virus removal membrane manufactured in the same conditions as in Manufacturing Example 5, having a membrane area of 3 cm$^2$, and the time taken for filtration of a total amount of 25 mL of the solution prepared was 180 minutes as represented in FIG. 11. The results obtained by conversion of each result of the present test into the total amount to be filtered off per membrane area are represented in FIG. 9.

Comparative Example 3

The same solution as the solution prepared in Example 3 was filtered directly by a virus removal membrane without use of a prefilter, at a constant pressure of 3 bar, and only about 15.9 mL of the solution could be filtered even for 3 hours as represented in FIG. 11. It was expected from such a curve that the time taken for filtration of a total amount of 25 mL of the solution was 1850 hours or more. The multimers here loaded to the virus removal membrane were in an amount of 0.5 g per 1 m$^2$. The results obtained by conversion of each result of the present test into the total amount to be filtered off per membrane area are represented in FIG. 9.

Example 4

The same method as in Example 1 was performed to prepare 25 mL of a solution having a final globulin concentration of 30 mg/mL, a sodium chloride concentration of 50 mmol/L, and a pH of 5.3, and solution A was added to the solution so that 0.3 mg of multimers was contained.

Figure 12:
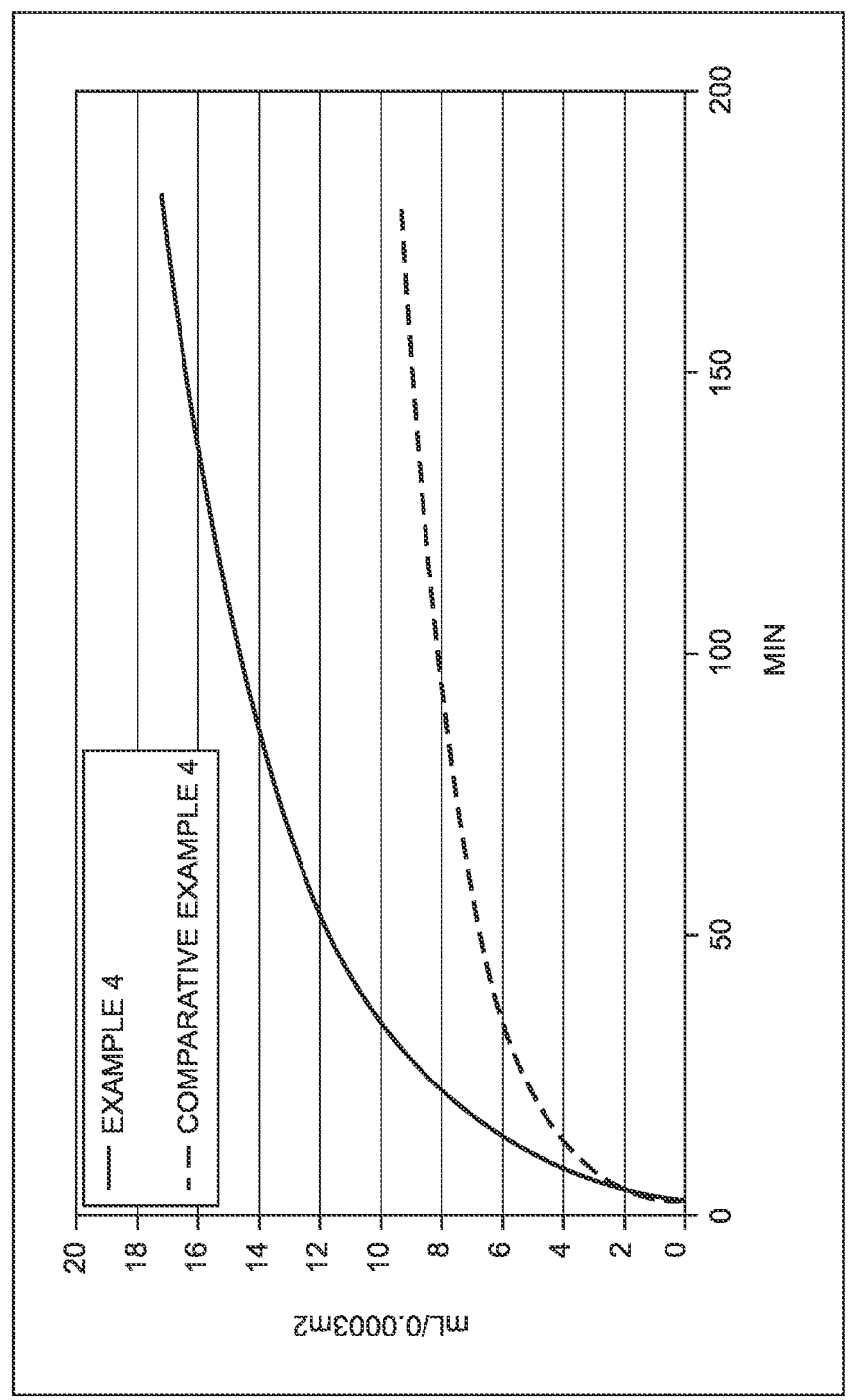
FIG. 12 is a graph representing a temporal change in the total amount of filtrate, by each virus removal membrane according to Example 4 of the present invention and Comparative Example 4.

The prefilter prepared was a membrane syringe filter NY (Corning) having a membrane area of 4.8 cm$^2$, including nylon and having a pore size of 0.2 μm, and filtration at a constant pressure of 0.2 bar was performed. Two of the prefilters were prepared, and the first filter was again connected to the second filter at a position where 12.5 mL of a liquid to be treated, corresponding to the half the total amount of the liquid, was filtered. The resulting filtrate was filtered at a constant pressure of 3 bar by a virus removal membrane manufactured in the same conditions as in Manufacturing Example 5, having a membrane area of 3 cm$^2$, and 17.2 mL of the filtrate could be filtered at 3 hours as represented in FIG. 12. It could be presumed based on such a curve that the time taken for a total amount of 25 mL of the solution was about 47 hours. The results obtained by conversion of each result of the present test into the total amount to be filtered off per membrane area are represented in FIG. 9.

Comparative Example 4

The same solution as the solution prepared in Example 4 was filtered directly by a virus removal membrane without use of a prefilter, at a constant pressure of 3 bar, and only about 9.6 mL of the solution could be filtered even for 3 hours as represented in FIG. 12. It was expected from such a curve that the time taken for filtration of a total amount of 25 mL of the solution was 4900 hours or more. The multimers here loaded to the virus removal membrane were in an amount of 1 g per 1 m$^2$. The results obtained by conversion of each result of the present test into the total amount to be filtered off per membrane area are represented in FIG. 9.

Example 5

The same method as in Example 1 was performed to prepare 25 mL of a solution having a final globulin concentration of 30 mg/mL, a sodium chloride concentration of 50 mmol/L, and a pH of 5.3, and solution A was added to the solution so that 1.03 mg of multimers was contained.

Figure 13:
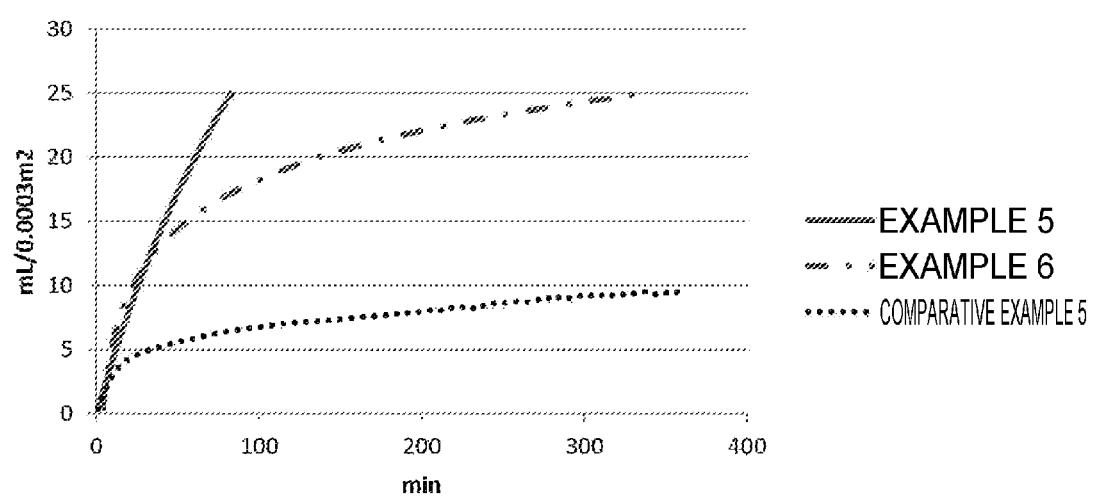
FIG. 13 is a graph representing a temporal change in the total amount of filtrate, by each virus removal membrane according to Examples 5 and 6 of the present invention, and Comparative Example 6.

The prefilter prepared was Durapore (Merck KGaA) having a membrane area of 10 cm$^2$, including polyvinylidene fluoride (PVDF), and having a pore size of 0.1 μm. The prefilter was linked upstream of a virus removal membrane manufactured in the same conditions as in Manufacturing Example 5, having a membrane area of 3 cm$^2$, and filtration was made at a constant pressure with being adjusted so that the pressure applied to the virus removal membrane was 3 bar. It was thus found that the time taken for filtration of a total amount of 25 mL of the solution prepared was 84 minutes as represented in FIG. 13. The results obtained by conversion of each result of the present test into the total amount to be filtered off per membrane area are represented in FIG. 14.

Example 6

The prefilter prepared for the same solution as in Example 5 was one including two of Virosart Max (Sartorius Stedim Japan K. K.) connected in series, in which three layers having a membrane area of 5 cm$^2$, including polyamide and having a pore size of 0.1 μm were stacked. The prefilter was linked upstream of a virus removal membrane manufactured in the same conditions as in Manufacturing Example 5, having a membrane area of 3 cm$^2$, and filtration was made at a constant pressure with being adjusted so that the pressure applied to the virus removal membrane was 3 bar. It was thus found that the time taken for filtration of a total amount of 25 mL of the solution prepared was 340 minutes as represented in FIG. 13. The results obtained by conversion of each result of the present test into the total amount to be filtered off per membrane area are represented in FIG. 14.

Comparative Example 5

The same solution as in Example 5 was filtered, without use of a prefilter, by one linked upstream of a virus removal membrane manufactured in the same conditions as in Example 5, having a membrane area of 3 cm$^2$, at a constant pressure with adjustment so that the pressure was 3 bar, and only about 9.6 mL of the solution could be filtered even for 6 hours as represented in FIG. 13. It was expected from such a curve that the time taken for filtration of a total amount of 25 mL of the solution was 150,000 hours or more. The multimers here loaded to the virus removal membrane were in an amount of 3.4 g per 1 m$^2$. The results obtained by conversion of each result of the present test into the total amount to be filtered off per membrane area are represented in FIG. 14.

(Virus Removal Ability of Virus Removal Membrane in Presence of Multimer)

(1) Preparation of Multimer- and Virus-Containing Protein Solution

Polyclonal antibodies (human IgG) (Venoglobulin-IH, manufactured by Benesis Corporation) were used to provide 300 mL of an antibody solution that was diluted with water for injection (Otsuka Pharmaceutical Co., Ltd.) so as to have an antibody concentration of 30 mg/mL. The salt concentration was adjusted to 0.1 mol/L by use of an aqueous 1 mol/L NaCl solution. Furthermore, the hydrogen-ion exponent (pH) was adjusted to 4.0 by use of 0.1 mol/L HCl or 0.1 mol/L NaOH, to provide a protein solution. Solution A was added to the resulting protein solution so that the protein solution contained 0.1125 mg of multimers, and porcine parvovirus (PPV; Japanese Association of Veterinary Biologics) was further added in a concentration of 3.0% by vol and well stirred to provide a multimer- and virus-containing protein solution.

Example 7

The multimer- and virus-containing protein solution was subjected to dead-end filtration at a filtration pressure of 196 kPa, by Virosart Max (Sartorius Stedim Japan K. K.) as a prefilter being linked to the front stage of a manufactured virus removal membrane having a membrane area of 0.0003 m$^2$. No viruses were detected with respect to the filtrate obtained by filtration of the total amount of the solution.

Comparative Example 6

The same solution as in Example 1 was subjected to dead-end filtration without use of a prefilter, but a rapid reduction in filtration rate was caused at a point of time of filtration of about 60 mL of the solution in the middle and the rest of filtration was difficult to perform, and therefore filtration was interrupted at a point of time of filtration of about 80 mL of the solution. Viruses were detected in the filtrate obtained until such interruption, and the virus removal membrane could not completely remove viruses. If the total amount of the solution was here filtered, 0.375 g of multimers per 1 m² of the virus removal membrane would be loaded to the virus removal membrane.

REFERENCE SIGNS LIST 1 primary surface
2 secondary surface
10 virus removal membrane

The invention claimed is:

1. A method for filtering a protein-containing liquid containing protein at a concentration of 20 mg/mL or more and 100 mg/mL or less, the method comprising:
 prefiltering the protein-containing liquid with a prefilter having a pore size of 0.08 µm to 0.25 µm and comprising a hydrophobic resin, and
 filtering the prefiltered protein-containing liquid with a virus removal membrane comprising a synthetic polymer to remove the virus,
 wherein:
  the protein-containing liquid before conducting the prefiltering comprises 0.25 g or more of a trimer or higher multimer of the proteins having an average diameter of less than 100 nm, per 1 m² of the virus removal membrane; and
  the hydrophobic resin hydrophobically interacts with and adsorbs the trimers or higher multimers of the proteins.

2. The method according to claim 1, wherein the prefilter comprises a material selected from the group consisting of a polyamide resin, a polysulfone-based resin and a fluororesin.

3. The method according to claim 2, wherein the prefilter comprises polyether sulfone or polyvinylidene fluoride.

4. The method according to claim 1, wherein the protein-containing liquid before conducting the prefiltering further comprises a particulate substance which is a multimer of the proteins and which has an average diameter of 100 nm or more.

5. The method according to claim 1, further comprising conducting diafiltration of the protein-containing liquid, before the prefiltering.

6. The method according to claim 1, further comprising conducting ultrafiltration of the protein-containing liquid, before the prefiltering.

7. The method according to claim 5, not further comprising ultrafiltration and diafiltration, after the diafiltration and before the prefiltering with the prefilter and the filtering with the virus removal membrane.

8. The method according to claim 1, further comprising a conducting filtration by use of a tangent flow filtration apparatus, before the prefiltering.

9. The method according to claim 1, further comprising stirring the protein-containing liquid for two hours or more, before the prefiltering.

10. The method according to claim 1, wherein there is no other method step between the prefiltering and the virus removal.

11. The method according to claim 1, wherein the prefiltering and the virus removal are successively performed.

12. The method according to claim 1, wherein the prefilter is a sheet-shaped filter.

13. The method according to claim 1, wherein the prefilter comprises a multi-layer membrane.

14. The method according to claim 1, wherein the prefilter comprises a multi-layer membrane where each layer is different in filter pore size.

15. The method according to claim 1, wherein a viscosity of the protein-containing liquid filtered by the prefilter is lower than a viscosity of the protein-containing liquid before filtration by the prefilter.

16. The method according to claim 1, wherein the protein comprises an antibody.

17. The method according to claim 1, wherein the protein comprises a monoclonal antibody.

18. The method according to claim 1, wherein the virus removal membrane comprises a fluororesin.

19. The method according to claim 18, wherein the virus removal membrane comprises polyvinylidene fluoride.

20. The method according to claim 1, wherein a logarithmic removal rate (LRV) for parvovirus by the virus removal membrane is 4.0 or more.

21. The method according to claim 1, wherein the virus removal membrane comprises
 a primary surface to which the protein-containing liquid filtered by the prefilter is applied, and
 a secondary surface from which a liquid that permeates through the virus removal membrane is flowed,
 wherein, in the case where a solution containing gold colloids having a diameter of 20 nm is applied through the primary surface to the virus removal membrane to allow the virus removal membrane to capture the gold colloid for measurement of brightness in a cross section of the virus removal membrane, a value obtained by dividing a standard deviation of a value of an area of a spectrum of variation in the brightness by an average of the value of the area of the spectrum of variation in the brightness is 0.01 or more and 1.50 or less, and wherein a thickness of a portion where gold colloids having a diameter of 20 nm or more and 30 nm or less are captured in the cross section of the virus removal membrane in a wet state is 10 µm or more and 30 µm or less.

22. The method according to claim 1, wherein the protein-containing liquid before conducting the prefiltering has a hydrogen-ion exponent of 4.0 or more and 8.0 or less.

23. The method according to claim 1, wherein the protein-containing liquid before conducting the prefiltering has an ionic strength of 0 mmol/L or more and 300 mmol/L or less.

24. The method according to claim 1, wherein the protein-containing liquid before conducting the prefiltering comprises an additive comprising at least one selected from the group consisting of a sugar and a basic amino acid.

25. The method according to claim 1, wherein the prefilter is sterilizable-in-place.

26. The method according to claim 1, wherein the prefilter comprises a polyamide resin, a polysulfone-based resin, and/or a fluororesin.

27. The method according to claim 1, wherein the virus removal membrane comprises polyvinylidene fluoride.

28. The method according to claim 1, wherein the virus removal membrane has hydrophilic graft chains.

29. The method according to claim 1, wherein the virus removal membrane comprises hydrophobic thermoplastic crystal resin and has hydrophilic graft chains.

* * * * *